(12) United States Patent
Kuwabata et al.

(10) Patent No.: US 7,880,144 B2
(45) Date of Patent: Feb. 1, 2011

(54) LIQUID MEDIUM FOR PREVENTING CHARGE-UP IN ELECTRON MICROSCOPE AND METHOD OF OBSERVING SAMPLE USING THE SAME

(75) Inventors: Susumu Kuwabata, Ibaraki (JP); Tsukasa Torimoto, Nagoya (JP)

(73) Assignees: Juridical Foundation Osaka Industrial Promotion Organization c/o Mydome Osaka, Osaka (JP); Osaka University, Osaka (JP); Hitachi High-Technologies Corporation, Tokyo (JP)

( * ) Notice: Subject to any disclaimer, the term of this patent is extended or adjusted under 35 U.S.C. 154(b) by 257 days.

(21) Appl. No.: 12/223,012

(22) PCT Filed: Jan. 19, 2007

(86) PCT No.: PCT/JP2007/050816

§ 371 (c)(1),
(2), (4) Date: Nov. 14, 2008

(87) PCT Pub. No.: WO2007/083756

PCT Pub. Date: Jul. 26, 2007

(65) Prior Publication Data

US 2009/0173882 A1 Jul. 9, 2009

(30) Foreign Application Priority Data

Jan. 20, 2006 (JP) .............................. 2006-012597

(51) Int. Cl.
*H01J 37/26* (2006.01)
*G21K 5/08* (2006.01)
(52) U.S. Cl. ..................... 250/311; 250/306; 250/307; 250/440.11; 250/310
(58) Field of Classification Search ................ 250/306, 250/307, 309, 310, 311, 440.11, 441.11, 250/442.11; 430/296
See application file for complete search history.

(56) References Cited

U.S. PATENT DOCUMENTS 5,378,498 A * 1/1995 Shu et al. .................... 427/240

(Continued)

FOREIGN PATENT DOCUMENTS

JP 57-147857 9/1982

(Continued)

OTHER PUBLICATIONS

Pernak, J., et al., "New Ionic Liquids and Their Antielectrostatic Properties", Industrial & Engineering Chemistry Research, May 30, 2001, pp. 2379-2383, vol. 40 No. 11, The American Chemical Society for Applied Chemistry & Chemical Engineering.

(Continued)

*Primary Examiner*—Jack I Berman
*Assistant Examiner*—Nicole Ippolito Rausch
(74) *Attorney, Agent, or Firm*—McDermott Will & Emery LLP

(57) ABSTRACT

An object of the present invention is to provide a medium; a specimen; a method for preparing the specimen; a method for observing the specimen; a sample cell; and an electron microscope capable of easily solving the problem of charge-up and further capable of observing a real shape or the like of a sample with a SEM, a TEM or the like. For the purpose of achieving the above-described object, the present invention uses an electrical conductivity-imparting liquid medium, for use in a microscope, which includes an ionic liquid as an essential component thereof and is impregnated into the entirety of a SEM or TEM sample or applied to the observation surface of a SEM or TEM sample to impart electrical conductivity at least to the observation surface of the sample. According to the present invention, the charge built up on the sample surface can be released simply by impregnating or coating the sample with the ionic liquid, and hence the problem of charge-up can be easily solved. Further, even when a sample impregnated or coated with the ionic liquid is placed under vacuum, the ionic liquid is not evaporated from the sample, and hence a biological sample can be observed as it is in an original shape.

43 Claims, 10 Drawing Sheets

U.S. PATENT DOCUMENTS

| | | | |
|---|---|---|---|
| 6,929,934 B1 * | 8/2005 | Korchev et al. | 435/173.1 |
| 7,309,558 B1 * | 12/2007 | Michel et al. | 430/137.1 |
| 2005/0065020 A1 * | 3/2005 | Holbrey et al. | 502/162 |
| 2007/0164216 A1 * | 7/2007 | Fedorov | 250/309 |

FOREIGN PATENT DOCUMENTS

| | | |
|---|---|---|
| JP | 02-015546 | 1/1990 |
| JP | 03-043945 | 2/1991 |
| JP | 03-163736 | 7/1991 |
| JP | 6-122869 | 5/1994 |
| JP | 2001-517205 | 10/2001 |

OTHER PUBLICATIONS

Pernak, J., et al., "Ionic Liquids with Symmetrical Dialkoxymethyl-Substituted Imidazolium Cations", Chemistry—A European Journal, Jul. 19, 2004, pp. 3479-3485, vol. 10 No. 14, Wiley-VCH, Weinheim, Germany.

Pernak, J., "Synthesis and Properties of Chiral Ammonium-Based Ionic Liquids", Chemistry—A European Journal, Jul. 18, 2005, pp. 4441-4449, vol. 11 No. 15, Wiley-VCH, Weinheim, Germany.

Pernak, J., "Phosphonium Acesulfamate Based Ionic Liquids", European Journal of Organic Chemistry, Feb. 11, 2005, pp. 650-652, vol. 2005 No. 4, Wiley-VCH, Weinheim, Germany.

* cited by examiner

LIQUID MEDIUM FOR PREVENTING CHARGE-UP IN ELECTRON MICROSCOPE AND METHOD OF OBSERVING SAMPLE USING THE SAME

RELATED APPLICATIONS

This application is the U.S. National Phase under 35 U.S.C. §371 of International Application No. PCT/JP2007/050816, filed on Jan. 19, 2007, which in turn claims the benefit of Japanese Application No. 2006-012597, filed on Jan. 20, 2006, the disclosures of which Applications are incorporated by reference herein.

TECHNICAL FIELD

The present invention relates to a liquid medium that is used, in the observation of a sample with an electron microscope such as a scanning electron microscope or a transmission electron microscope, to prevent the charge-up of the observation surface of the sample, and a method of observing a sample by using the liquid medium.

BACKGROUND ART

In these days, high-precision observation of nano-level or micro-level microstructures has been requested, and in general, a scanning electron microscope (hereinafter referred to as SEM) is used as an apparatus for observing microstructures or the like.

Here, it may be noted that a SEM is a type of electron microscope that can display a three-dimensional image of an observation sample wherein the observation sample is irradiated with an electron beam while the electron beam is scanning the sample; secondary electrons, reflected electrons, characteristic X-rays, fluorescence and the like are generated by the collision of the electron beam with the observation sample; among these, for example, the secondary electrons are detected by a detector, and the brightness corresponding to the electric charge of the detected electrons and the positional information about the electron-irradiated positions are processed to derive the three-dimensional image of the observation sample.

In general, the secondary electron emission gain that represents a ratio between the incident amount of the primary electrons irradiating the observation sample and the emission amount of the secondary electrons emitted from the observation sample by the irradiation of the primary electrons depends on the primary electron acceleration voltage, namely, the incidence energy of the primary electrons. As shown in FIG. 3, the relation between the secondary electron emission gain and the primary electron acceleration voltage is such a function that the secondary electron emission gain has a maximum value in the intermediate region of the primary electron acceleration voltage, and the secondary electron emission gain comes close to zero as the primary electron acceleration voltage comes close to zero or approaches infinity. Here, the primary electron acceleration voltage region where the secondary electron emission gain is 1 or more is designated as the intermediate region B; and of the two primary electron acceleration voltage regions where the secondary electron emission gain is 1 or less, the region where the primary electron acceleration voltage is smaller than that of the intermediate region is designated as the lower region A, and of the two primary electron acceleration voltage regions where the secondary electron emission gain is 1 or less, the region where the primary electron acceleration voltage is larger than that of the intermediate region is designated as the higher region C. Accordingly, in the lower region A and the higher region C of the primary electron acceleration voltage, the secondary electron emission gain is 1 or less and the incident amount of the primary electrons is larger than the emission amount of the secondary electrons, and hence on the sample surface, the amount of electrons having negative charge is relatively increased and the sample surface is negatively charged as the primary electrons are made incident on the sample surface. Additionally, in the intermediate region B of the primary electron acceleration voltage, the secondary electron emission gain is 1 or more, the incident amount of the primary electrons is smaller than the emission amount of the secondary electrons, and hence the amount of the electrons is relatively decreased on the sample surface and the sample surface is positively charged as the primary electrons are made incident on the sample surface.

When the sample to be observed is an electrical conductor and is grounded, the charge built up as described above can be released toward outside the sample. However, when the sample is a body made up of an insulating material or a body surrounded by an insulating material, the charge built up on the surface of the sample cannot be released, and hence an observation of the sample with a SEM is not permitted precisely observing the image of the sample because of such charge-up. In particular, when the primary electron acceleration voltage falls within the intermediate region B, the emission amount of the secondary electrons is larger relative to the incident amount of the primary electrons, and hence the SEM observation image is poor in image shading and the image is displayed to be white as a whole. Accordingly, attempts have been made to prevent the charge-up by decreasing the incident amount of the primary electrons. However, when the incident amount of the primary electrons is decreased, the image resolution is decreased to blur the image. On the other hand, when the primary electron acceleration voltage falls within the lower region A or the higher region C, the sample surface is negatively charged, and hence the negative charge built up on the sample surface deforms the trajectory of the primary electrons incident from the electron gun to inhibit accurate measurement.

Accordingly, when the sample surface to be observed is made up of an insulating material, attempts have been made, for the purpose of preventing the charge-up, to release the charge built up on the sample surface by vapor deposition, on the sample surface, of carbon (C), aluminum (Al), platinum (Pt), or the like.

Additionally, Patent Document 1 has proposed, for the purpose of preventing the charge-up, a scanning electron microscope in which the sample surface is irradiated with the primary electrons at an acceleration voltage at which the secondary electron emission gain of 1 is attained (Patent Document 1). Such an apparatus provides a secondary electron emission gain of 1, namely, the incident amount of the primary electrons is equal to the emission amount of the secondary electrons, and hence no charge is built up on the sample surface to enable prevention of the charge-up.

Further, Patent Document 2 has proposed a technique in which the back side opposite to the sample surface is irradiated with an ion shower, and thus the sample surface negatively charged with electrons is neutralized by the ion shower (Patent Document 2).

On the other hand, when microstructures are observed, observation has also been conducted with a transmission electron microscope (hereinafter referred to as TEM) in addition to a SEM.

Here, it may be noted that a TEM is a type of electron microscope that can display a two-dimensional image of an observation sample wherein the observation sample is irradiated with an electron beam, the electron beam is allowed to transmit through the sample, the transmission amount of the electron beam that varies with the observation position of the observation sample is detected, and the two-dimensional image display of the sample can be conducted by processing the variation of the transmission amount and the observation positions irradiated with the electron beam.

Because the image is observed by irradiating the observation sample with electrons and by allowing the electrons to transmit through the sample, the observation is conducted in such a way that the target sample is cut as thin as possible or the target sample is thinly applied on an electron-transmitting film. Additionally, a sample for a TEM is sliced to a thickness of approximately 100 nm or less so as to allow electrons to transmit through the sample. Further, when a sample is, for example, a biological sample, such a biological sample generally contains a large water content, the water content thereof is evaporated instantly after the sample is placed under vacuum and the shape of the sample is also deformed, and hence complete drying of the sample is needed.

Patent Document 1: JP Patent Publication (Kokai) No. 3-163736 (1991)

Patent Document 2: JP Patent Publication (Kokai) No. 2-15546 (1990)

DISCLOSURE OF THE INVENTION

However, in the observation with a SEM, for a method in which the charge-up of the sample surface is prevented by vapor deposition of carbon (C), aluminum (Al), platinum (Pt) or the like on the surface of the sample made up of an insulating material, a separate vapor deposition step is required to be conducted before the observation of the sample, and hence the steps become complicated and a vapor deposition apparatus and the like are required to be prepared.

Additionally, as described in Patent Document 1, in a SEM in which the sample surface is irradiated with primary electrons at an acceleration voltage at which the secondary electron emission gain of 1 is attained, although the secondary electron emission gain is maintained at 1 when the portion irradiated with the electron beam is a portion made up of a certain material, the secondary electron emission gain is varied when the portion irradiated with the electron beam is moved to a portion made up of a different material, and accordingly, no complete prevention of the charge-up is possible. At the instant when the portion irradiated with the electron beam is moved to the portion made up of the different material, a revision may be made so as to render the secondary electron emission gain to be 1; however, for that purpose, a revision technique capable of conducting such a revision is needed to be provided, and hence there has been a problem that the measurement becomes complicated.

Further, for the SEM in which the back side opposite to the sample surface is irradiated with an ion shower and thus the sample surface negatively charged by the electron irradiation is neutralized by the ion shower (Patent Document 2), there has been a problem that the sample surface is irradiated with the ion shower, and hence the sample itself is processed by the ion shower to be damaged.

Additionally, both in the SEM observation and in the TEM observation, the water content in a biological sample is required to be completely evaporated to be dried, and hence there has been a problem that the shape or the like as it is naturally possessed by a biological object cannot be observed. Accordingly, there have been made attempts in which a sample is dried by freeze drying or critical point drying while the shape possessed by a sample is maintained as much as possible; however, there has been a problem that it is difficult to prepare a sample while the shape of the sample is completely maintained and such a preparation takes time and labor.

Accordingly, a first object of the present invention is to provide a liquid medium capable of simply solving the problem of charge-up, and additionally, capable of allowing easy preparation of a sample, and capable of allowing observation of the shape or the like of a sample, as it is, with a SEM, a TEM or the like, and to provide an observation method using the liquid medium. Additionally, a second object of the present invention is to provide a specimen capable of solving the above-described problems and to provide a preparation method of the specimen. Further, a third object of the present invention is to provide a sample cell capable of solving the above-described problems, and a fourth object of the present invention is to provide an electron microscope capable of solving the same problems as described above.

The present inventors made a diligent study in view of the above-described problems, and consequently discovered that when an ionic liquid is impregnated into a SEM sample or a TEM sample or applied to the surface of the sample, electrons emitted from an electron gun built in a SEM or TEM transmit through the ionic liquid filled in the sample although the incident energy of the electrons is not so high, consequently secondary electrons or transmitted electrons can be detected, and observation with a SEM, a TEM or the like is thereby enabled, and that the charges built up on the sample surface is released through the ionic liquid and no problem of charge-up occurs. An ionic liquid as referred to herein means a liquid that is liquid at ordinary temperatures and is composed of ions. Such an ionic liquid is characterized by properties such as nonvolatility, noncombustibility, thermal stability, chemical stability, high ionic conductivity and resistance to electrolysis. Accordingly, even when a sample impregnated or coated with an ionic liquid is placed under vacuum, the ionic liquid is scarcely volatilized from the sample, and hence, in particular, when a biological sample is observed, the biological sample undergoes no contraction and other deformations and the shape of the biological sample can be observed as it is.

Accordingly, an aspect of the present invention resides in a charge-up preventing liquid medium for electron microscope, characterized in that the liquid medium includes as an essential component thereof an ionic liquid that is composed of a cation and an anion and is difficultly or scarcely volatilized under vacuum, and is impregnated into the entirety of a sample for a scanning electron microscope (SEM) or a sample for a transmission electron microscope (TEM) or applied to the electron irradiation surface of the sample to impart electrical conductivity at least to the electron irradiation surface.

Additionally, when an observation object is impregnated or coated with an ionic liquid, the observation object is converted into a specimen observable with an electron microscope such as a SEM or a TEM. Accordingly, a specimen according to the present invention is a specimen for observation with an electron microscope, and is characterized by including the observation object and an ionic liquid that includes a cation and an anion and is liquid during the observation with the electron microscope. Here, the statement that the ionic liquid is liquid during the observation with the electron microscope means that the ionic liquid is not volatilized at all or is scarcely volatilized even under the vacuum in the vacuum chamber of the SEM, TEM or the like and maintains the liquid state, namely that the ionic liquid is not volatilized at all or is scarcely volatilized, and further does not boil during the observation with the SEM, TEM or the like. Additionally, examples of the electron microscope as referred to herein include a SEM and a TEM, and also include any apparatus that permits observing an observation object under vacuum.

The specimen can also be prepared according to the below-described methods. Accordingly, a first method of preparing a specimen according to the present invention is a method for preparing a specimen for observation with an electron microscope, and is characterized by including an immersion step of immersing a water-containing biological sample in an ionic liquid that includes a cation and an anion and is liquid during the observation with the electron microscope and a drying step of removing the water contained in the biological sample by placing under vacuum the biological sample having been immersed in the ionic liquid.

Additionally, when the ionic liquid is diluted with a solvent more easily volatile than the ionic liquid, even for an observation object having a fine structure, the coating with the ionic liquid can be made even in the interior of the fine structure thereof, and hence a satisfactory observation can be conducted. Accordingly, a second method of preparing a specimen according to the present invention is a method for preparing a specimen for observation with an electron microscope, and is characterized by including a dilution step of diluting an ionic liquid that includes a cation and an anion and is liquid during the observation with the electron microscope, with a solvent more easily volatile than the ionic liquid, a coating step of coating the observation object with the ionic liquid diluted with the solvent and a drying step of removing the solvent by placing under vacuum the observation object having been coated with the ionic liquid diluted with the solvent.

Further, by immersing an observation object in an ionic liquid and by applying electricity from a positive electrode and a negative electrode to the observation object, the behavior of the observation object can be observed; by using the below-described sample cell, the above-described behavior can be observed. Accordingly, a sample cell according to the present invention is a cell used for observation of a specimen with an electron microscope, and is characterized by including an ionic liquid that includes a cation and an anion and is liquid during the observation with the electron microscope, an insulating cell containing the ionic liquid, and the positive electrode and the negative electrode immersed in the ionic liquid.

Additionally, an electron microscope according to the present invention is an electron microscope used for observation of a specimen, and is characterized by including a vacuum chamber that houses the specimen and is evacuated to vacuum, an insulating cell that is housed in the vacuum chamber and is capable of containing an ionic liquid that is liquid during the observation with the electron microscope, a positive electrode and a negative electrode immersed in the ionic liquid filled in the insulating cell, an electron gun that irradiates the specimen with an electron beam and a detector that detects the secondary electrons generated by irradiating the specimen with the electrons from the electron gun.

Additionally, a method for observing a sample according to the present invention is a method for observing a sample by using the liquid medium with an electron microscope, and is characterized by including a step of imparting electrical conductivity at least to the observation surface of an observation object by impregnating the observation object with an ionic liquid that is composed of a cation and an anion and is not volatilized at all or is scarcely volatilized under vacuum, or by coating the observation surface of the observation object with the ionic liquid, and a step of obtaining an image of the observation object by irradiating with electrons the observation object having been impregnated or coated with the ionic liquid as described above and by detecting the secondary electrons or the transmitted electrons due to the irradiating electrons.

In the present invention, a biological object means one of the water-containing living things which include plants (flowers, leaves, stems, seeds and the like) as well as animals.

According to the charge-up preventing liquid medium for electron microscope, according to the present invention, the charges built up on the sample surface can be easily released so as to solve the problem of charge-up. Further, according to the observation method using the liquid medium according to the present invention, even when a sample impregnated or coated with an ionic medium is placed under vacuum, the ionic liquid is not volatilized from the sample, and hence, in particular, when a biological sample is observed, the shape of the biological sample free from contraction or the like can be observed as it is.

Additionally, according to the specimen and the preparation method thereof according to the present invention, the specimen is impregnated or coated with an ionic liquid, and hence the charge-up can be prevented in the same manner as described above, and the shape of the sample can be observed as it is.

Further, according to the sample cell and the electron microscope according to the present invention, a nonvolatile ionic liquid is injected into the cell and the ionic liquid expels the electrons to outside the sample, and hence the sample can be observed, similarly as above, in a manner free from the problem of charge-up.

DESCRIPTION OF SYMBOLS

Figure 1:
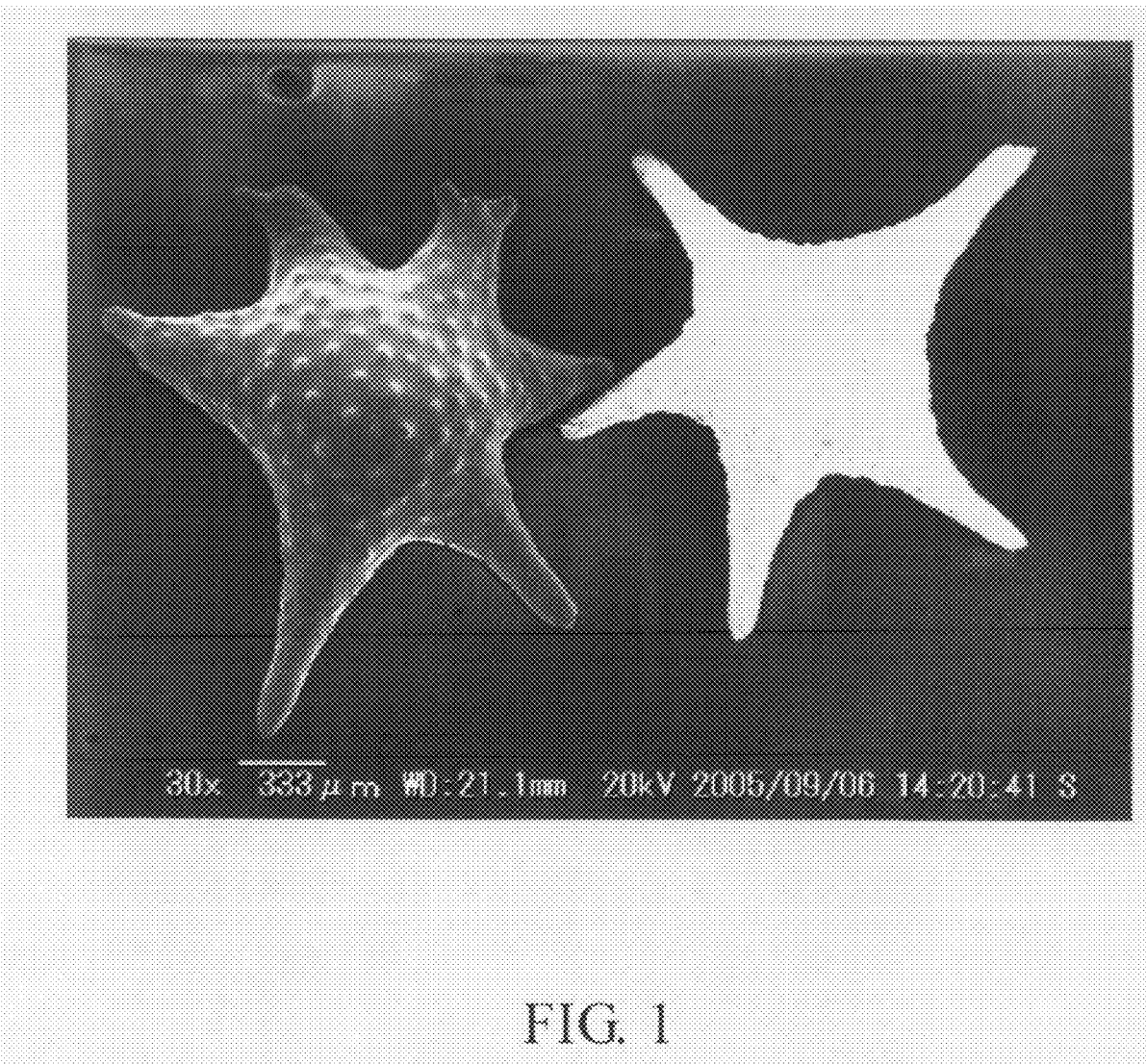
FIG. 1 is a SEM micrograph of a sample of star sand observed by means of an observation method according to the present invention.

1 Electron gun
2 Condenser lens
3 Scanning coil
4 Objective lens
5 Objective-lens aperture
6 Basal plate
7 Stage
8 Detector
9 Image amplifier
10 Display unit
11 Scanning circuit for driving electron optical system
12 Vacuum chamber
13 Insulating cell
14 Positive electrode
15 Negative electrode

BEST MODE FOR CARRYING OUT THE INVENTION

An aspect of the present invention resides in an electrical conductivity-imparting liquid medium, for use in microscope applications, which includes an ionic liquid as an essential component thereof and is impregnated into the entirety of a sample for a scanning electron microscope (SEM) or a transmission electron microscope (TEM) or is applied to the electron irradiation surface of the sample to impart electrical conductivity at least to the electron irradiation surface.

Hereinafter, description is made on the case where a SEM sample is impregnated or coated with an ionic liquid and the impregnated or coated sample is observed with a SEM. The outline of this case is such that the sample is cut or machined to a desired shape, then the shaped sample is impregnated with the ionic liquid to prepare a sample, the prepared sample is set in a SEM system, and the sample surface is observed by scanning an electron beam over the sample surface.

(Ionic Liquid)

Hereinafter, description is made on the ionic liquid contained in the electrical conductivity-imparting liquid medium to be impregnated into or applied to a sample. As described above, the ionic liquid is a liquid that is liquid at ordinary temperatures and/or under vacuum and is composed of ions. The ionic liquid is characterized by properties such as nonvolatility, noncombustibility, thermal stability, chemical stability, high ionic conductivity and resistance to electrolysis. In SEM and TEM observations, a sample is placed under vacuum, and hence preferably the ionic liquid impregnated into the sample is not volatilized (evaporated) at all or is scarcely volatilized (a). Additionally, if the primary electrons incident on the sample and the secondary electrons or the transmitted electrons emitted by the incidence of the primary electrons do not pass through the ionic liquid, neither a SEM image nor a TEM image is obtained, and hence the ionic liquid is required to have electron transmission capability (b).

Accordingly, when the sample as an observation object is observed with an electron microscope, preferably the ionic liquid is applied thinly to the sample surface or impregnated into the sample uniformly at least in the surface layer of the sample.

Additionally, for the purpose of preventing charge-up, the charge built up on the sample surface is required to be released to outside the sample, and hence the ionic liquid is required to have electronic conductivity (c).

Examples of the ionic liquid that satisfies the above (a) to (c) include the following ionic liquid.

For instance, the examples includes the ionic liquid characterized in that the ionic liquid is composed of $K^+A^-$ (1), wherein $K^+$ is N-alkylimidazolium cation represented by the general formula (2):

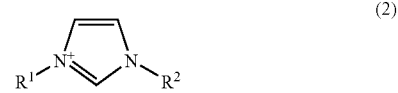

(2)

(in the formula, $R^1$ and $R^2$ each represent a $C_{1-10}$ alkyl group or a hydrogen atom, and may be the same or different from each other, with the proviso that $R^1$ and $R^2$ are not hydrogen atoms simultaneously), or $K^+$ is ammonium cation represented by the general formula (3):

(3)

(in the formula, $R^3$ represents a $C_{1-10}$ alkyl group or a hydrogen atom, and $R^3$s may be the same or different from each other), and $A^-$ is a tetrazole compound anion represented by the general formula (4):

(4)

(in the formula, $R^4$ represents a hydrogen atom, a $C_{1-10}$ alkyl group, a $C_{3-10}$ cycloalkyl group, a phenyl group, a hydroxyl group, a mercapto group, an amino group, a carboxyl group, a tetrazolyl group or a sulfonic acid group, and each of the groups represented by $R^4$ other than a hydrogen atom may have one or more substituents), or, $A^-$ is a triazole compound anion represented by the general formula (5):

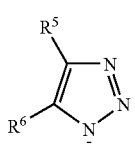

(5)

(in the formula, $R^5$ and $R^6$ each represent a hydrogen atom, a $C_{1-10}$ alkyl group, a $C_{3-10}$ cycloalkyl group, a phenyl group, a hydroxyl group, a mercapto group, an amino group, a carboxyl group, a tetrazolyl group or a sulfonic acid group, each of the groups represented by $R^5$ and $R^6$ other than a hydrogen atom may have one or more substituents, and $R^5$ and $R^6$ may be the same or different from each other), or $A^-$ is a triazole compound anion represented by the general formula (6):

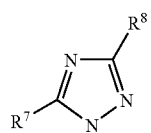

(6)

(in the formula, $R^7$ and $R^8$ each represent a hydrogen atom, a $C_{1-10}$ alkyl group, a $C_{3-10}$ cycloalkyl group, a phenyl group, a hydroxyl group, a mercapto group, an amino group, a carboxyl group, a tetrazolyl group or a sulfonic acid group, each of the groups represented by $R^7$ and $R^8$ other than a hydrogen atom may have one or more substituents, and $R^7$ and $R^8$ may be the same or different from each other).

The alkyl groups in N-alkylimidazolium cation represented by the above general formula (2) and ammonium cation represented by the above general formula (3) are each an alkyl group having 1 to 10 carbon atoms; preferable examples of such an alkyl group include a methyl group, an ethyl group, a propyl group, a butyl group, a pentyl group, a hexyl group, a heptyl group, an octyl group, a nonyl group and a decyl group.

Specific examples of N-alkylimidazolium cation include 1-methyl-3-methylimidazolium cation, 1-methyl-3-ethylimidazolium cation and 1-methyl-3-propylimidazolium cation.

Specific examples of ammonium cation include ammonium cation, trimethylammonium cation, ethyldimethylammonium cation, diethylmethylammonium cation, triethylammonium cation, tetramethylammonium cation, triethylmethylammonium cation and tetraethylammonium cation; preferable among these are triethylmethylammonium cation and tetraethylammonium cation.

For the tetrazole compound anion represented by the above general formula (4), the triazole compound anion represented by the above general formula (5) and the triazole compound anion represented by the above general formula (6), the following descriptions are presented: the alkyl groups in these anions are each an alkyl group having 1 to 10 carbon atoms, and examples of such an alkyl group include a methyl group, an ethyl group, a propyl group, a butyl group, a pentyl group, a hexyl group, a heptyl group, an octyl group, a nonyl group and a decyl group; the cycloalkyl groups are each a cycloalkyl group having 3 to 10 carbon atoms, and examples of such a cycloalkyl group include a cyclopropyl group, a cyclobutyl group, a cyclopentyl group, a cyclohexyl group, a cycloheptyl group, a cyclooctyl group, a cyclononyl group and a cyclodecyl group; and examples of the substituents that may be possessed by the respective groups other than a hydrogen atom include an alkyl group, a hydroxyl group, a mercapto group, an amino group and a carboxyl group.

Specific examples of the tetrazole compound anion include 1,2,3,4-tetrazole anion, 1H-5-carboxytetrazole anion, 1H-5-mercaptotetrazole anion, 1H-5-aminotetrazole anion, 1H-5-phenyltetrazole anion, 1H-tetrazole anion, 1H-5-methyltetrazole anion, 5,5'-bi-1H-tetrazole anion, 1,5-bi-1H-tetrazole anion and N-1H-tetrazol-5-yl-1H-tetrazol-5-amine anion; preferable among these are 1,2,3,4-tetrazole anion and 5,5'-bi-1H-tetrazole anion.

Specific examples of the triazole compound anion include 1,2,3-triazole anion, 4-mercapto-1,2,3-triazole anion, 1,2,4-triazole anion, 3-mercapto-1,2,4-triazole anion, 3-mercapto-5-methyl-1,2,4-triazole anion and 3,5-dimethyl-1,2,4-triazole anion; particularly preferable among these is 1,2,4-triazole anion.

The above-described anionic components are the anions obtained by eliminating a proton from each of the tetrazole compounds, the triazole compounds and the mixtures thereof.

Additionally, the anion $A^-$ is tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion.

Additionally, other specific examples of the ionic liquid include, for example, $K^+A^-$ composed of the below-described $A^-$ and $K^+$. Here, $A^-$ is bis(halogenated alkylsulfonyl)imide anion or bis(halogenated sulfonyl)imide anion represented by the general formula (7):

(7)

Examples of the halogen included in $R^9$ or $R^{10}$ bonded to an end of the above-described $A^-$ include fluorine, chlorine and bromine; particularly preferable among these is fluorine. Additionally, when $R^9$ or $R^{10}$ is a halogenated alkyl group, preferable is the halogenated alkyl group having 1 to 3 carbon atoms, and specific examples of the preferable halogenated alkyl groups include a trifluoromethyl group, a pentafluoroethyl group and a heptafluoropropyl group. The halogenated alkyl groups may be the same or different from each other, in the number of the carbon atoms. The possession of strongly electron withdrawing halogen atoms or halogenated alkyl groups provides the effects that the charge in the anion is dispersed, and the stability of the anion is thereby increased to facilitate the dissociation of the anion from the cation.

Preferable specific examples of the above-described $A^-$ include the following anions:

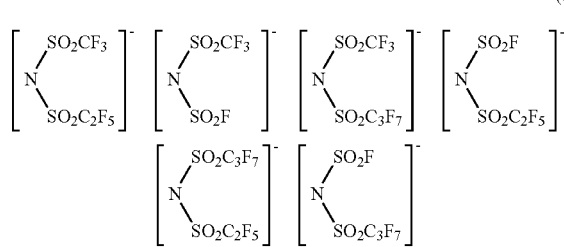
(8)

Additionally, $K^+$ is one of the quaternary ammonium ion and the quaternary phosphonium ion represented as follows:

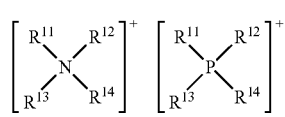
(9)

(wherein $R^{11}$, $R^{12}$, $R^{13}$ and $R^{14}$ are independent from each other, and represent an alkyl group, an aryl group, a heterocyclic group and an aralkyl group, respectively. These $R^{11}$, $R^{12}$, $R^{13}$ and $R^{14}$ may each contain a substituent and a heteroatom in the structure thereof; these $R^{11}$, $R^{12}$, $R^{13}$ and $R^{14}$ may be bonded to each other to form one or more rings, and further, these $R^{11}$, $R^{12}$, $R^{13}$ and $R^{14}$ may be bonded to the $R^{11}$, $R^{12}$, $R^{13}$ and $R^{14}$ of the adjacent cation to form a polymer shape.)

Examples of the alkyl group include straight chain or branched alkyl groups having at most 30 carbon atoms such as methyl, ethyl, n-propyl, isopropyl, n-butyl, isobutyl, sec-butyl, tert-butyl, pentyl, hexyl, heptyl, octyl, nonyl and decyl. Examples of the aryl group include phenyl, naphthyl, toluoyl and xylyl; the aryl group may have one or more substituents such as halogen atoms (F, Cl, Br, I), a hydroxyl group, alkoxy groups (such as methoxy, ethoxy, propoxy and butoxy), a carboxyl group, an acetyl group, a propanoyl group, a thiol group, alkylthio groups (such as methylthio, ethylthio, propylthio and butylthio), amino groups, alkylamino groups and dialkylamino groups. Examples of the heterocyclic group include pyridyl, thienyl, imidazolyl, pyrazolyl, oxazolyl, isooxazolyl, pyrrolidinyl, piperazinyl and morphorinyl. Examples of the aralkyl group include benzyl and phenethyl. Additionally, these $R^{11}$, $R^{12}$, $R^{13}$ and $R^{14}$ may be a ring such as pyrrolidinium and piperidinium formed by bonding between $R^{11}$, $R^{12}$, $R^{13}$ and $R^{14}$ in one molecule, and further may be a chain such as the structure shown by the general formula (10), formed by bonding of the $R^{11}$, $R^{12}$, $R^{13}$ and $R^{14}$ to the $R^{11}$, $R^{12}$, $R^{13}$ and $R^{14}$ of another adjacent cation.

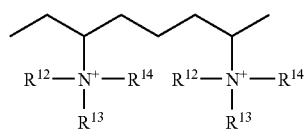
(10)

Specific examples of the preferable cation component in the ionic liquid are as follows.

Such examples include: trimethylhexylammonium, trimethylphenylammonium, trimethylcyclohexylammonium, dimethylethylhexylammonium, tetraethylammonium, trimethylbenzylammonium, trimethylvinylammonium, trimethyl(methoxycarbonylethyl)ammonium, trimethylethylammonium, trimethyl(hydroxyethyl)ammonium, triethylmethylammonium, diethylmethylhexylammonium, trimethyl(pentamethylphenyl)ammonium, triethylbenzylammonium, N-methyl-N-butylpiperidinium, N,N-dimethylpiperidinium, N-methyl-N-propylpiperidinium, N-methyl-N-butylpyrrolidinium, N-methyl-N-propylpyrrolidinium, N,N-dimethylpyrrolidinium, triethylbutylammonium, triethylamylammonium, tributylmethylammonium, tributylphenylammonium, tributylbenzylammonium, trimethylallylammonium, trimethylhexylphosphonium, trimethylphenylphosphonium, trimethylcyclohexylphosphonium, dimethylethylhexylphosphonium, tetraethylphosphonium, trimethylbenzylphosphonium, trimethylvinylphosphonium, trimethyl(methoxycarbonylethyl)phosphonium, trimethylethylphosphonium, trimethyl(hydroxyethyl)phosphonium, triethylmethylphosphonium, diethylmethylhexylphosphonium, trimethyl(pentamethylphenyl)phosphonium, triethylbenzylphosphonium, triethylbutylphosphonium, triethylamylphosphonium, tributylmethylphosphonium, tributylphenylphosphonium, tributylbenzylphosphonium, trimethylallylphosphonium, and the phosphoniums listed below:

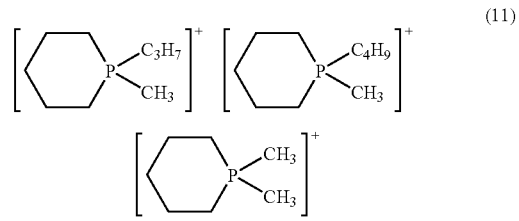
(11)

Further, other specific examples of the ionic liquid include ionic liquids represented by $K^+A^-$, and characterized in that $K^+$ is the cation represented by the general formula (12),

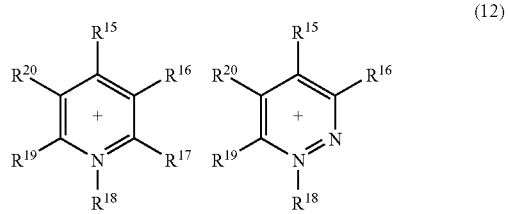
(12)

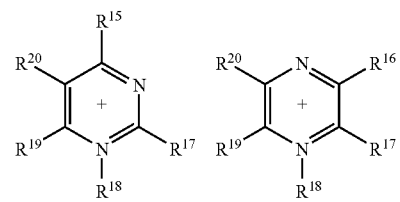

-continued

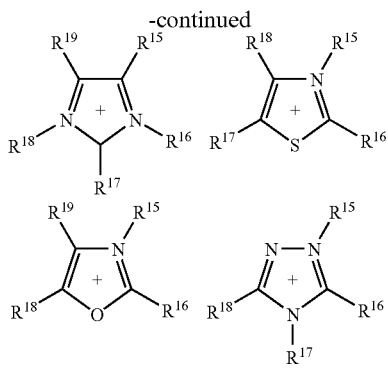

(in the formula, $R^{15}$ to $R^{20}$ may be the same or different from each other; these $R^{15}$ to $R^{20}$ are directly bonded through a single bond or a double bond, and are each independently or simultaneously a hydrogen atom, a halogen atom or a $C_{1-8}$ alkyl group; preferably this alkyl group may be partially or fully substituted with F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ (in the formulas, $1<n<6$ and $0<x\leq13$)), and $A^-$ is represented by $[B(OR^{21})_n(OR^{22})_m(OR^{23})_o(OR^{24})_p]^-$ (in the formula B is boron; $A^-$ is an anion selected from the group of the anions satisfying $0\leq n, m, o, p \leq 4$ and $m+n+o+p=4$; in the formula, $R^{21}$ to $R^{24}$ may be different from each other or the same and are bonded to each other through a single bond or a double bond; additionally, each of $R^{21}$ to $R^{24}$ is an aromatic ring selected from the group consisting of phenyl, naphthyl, anthracenyl and phenanthrenyl unsubstituted or substituted singly or simultaneously with $C_nF_{(2n+1-x)}H_x$ (in the formula, $1<n<6$ and $0<x\leq13$) or halogen (F, Cl or Br), each of $R^{21}$ to $R^{24}$ is an aromatic heterocycle selected from the group consisting of pyridyl, pyrazyl and pyrimidyl unsubstituted or substituted with $C_nF_{(2n+1-x)}H_x$ (in the formula, $1<n<6$ and $0<x\leq13$) or halogen (F, Cl or Br), or each of $R^{21}$ to $R^{24}$ is a $C_{1-8}$ alkyl group (preferably this alkyl group may be partially or fully substituted with F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ (in the formulas, $1<n<6$ and $0<x\leq13$)).

Additionally, other specific examples of the ionic liquid include the ionic liquid represented by the general formula (13):

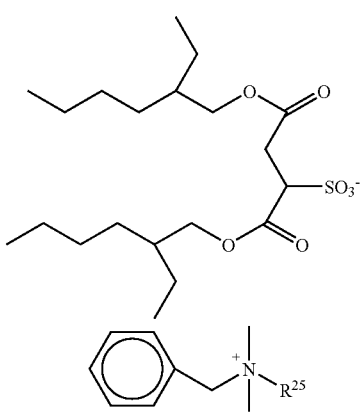

or the ionic liquid represented by the general formula (14):

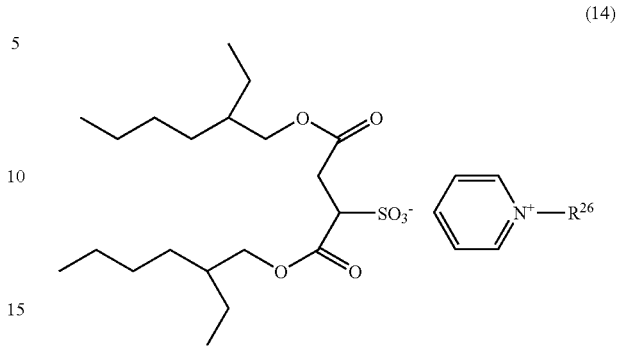

The anion in the general formulas (13) and (14) is bis-2-ethylhexyl sulfosuccinate anion, which includes two 2-ethylhexyl groups as alkyl groups. In this way, sulfosuccinate anion containing two branched chain alkyl groups each having 8 carbon atoms is used in the ionic liquid; however, in the case where the alkyl group is a straight chain, the melting point is equal to or higher than room temperature, or the viscosity of the produced compound is extremely high. Additionally, even when the alkyl group is a branched chain, in the case where the number of the carbon atoms is 9 or more, the viscosity of the produced compound is extremely high, and on the other hand, in the case where the number of the carbon atoms is 7 or less, the melting point is equal to or higher than room temperature.

Additionally, the cation $K^+$ in the general formula (13) is benzyldimethylalkylammonium cation, and $R^{25}$ in the same formula represents an alkyl group having 8 to 20 carbon atoms. Specific examples of such an alkyl group ($R^{25}$) include straight chain or branched chain alkyl groups such as an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an eicosyl group; particularly preferable among these is a dodecyl group in terms of low viscosity and low melting point.

Additionally, the cation $K^+$ in the general formula (14) is alkylpyridinium cation, and $R^{26}$ in the same formula represents an alkyl group having 12 to 18 carbon atoms. Specific examples of such an alkyl group ($R^{26}$) include a straight chain or branched chain dodecyl group, a straight chain or branched chain tridecyl group, a straight chain or branched chain tetradecyl group, a straight chain or branched chain pentadecyl group, a straight chain or branched chain hexadecyl group and a straight chain or branched chain heptadecyl group and a straight chain or branched chain octadecyl group; particularly preferable among these is a hexadecyl group in terms of low viscosity and low melting point.

As described above, description has been made on the ionic liquids, and the above-described ionic liquids are presented as illustrative examples; as long as ionic liquids satisfy part of or all of the above-described (a) to (c), and are liquid during observation, such ionic liquids can be used as the ionic liquid contained in the electrical conductivity-imparting liquid medium of the present invention.

Additionally, the above-described specific ionic liquids are used as the liquid medium for preventing charge-up in electron microscope according to the present invention, and can be used not only as such a medium but also for the specimen, the method for preparing the specimen, the sample cell, the electron microscope and the method for preparing a sample, according to the present invention.

(Specimen and the Method for Preparing the Specimen)

Next, description is made on the specimen observed with an electron microscope such as a SEM or a TEM. The specimen according to the present invention includes an observation object and an ionic liquid, and the ionic liquid includes a cation and an anion and is liquid during the observation with an electron microscope. When a specimen prepared in this way is used, because the observation object is coated or impregnated with the ionic liquid that is not volatilized even when placed in the sample chamber, under vacuum, of an electron microscope such as a SEM and has nonvolatility, the charge built up on the surface of the insulating observation object can be released to outside the observation object owing to the electrical conductivity of the ionic liquid and thus the charge-up can be prevented. Additionally, no adverse effects are exerted on the system such as a SEM.

When the specimen according to the present invention is prepared, a biological sample containing a large water content may be placed under vacuum and vacuum dried, and used as an observation object. Additionally, the ionic liquid diluted with a solvent such as alcohol, benzene, toluene, acetone, methyl ethyl ketone, methylene chloride, chloroform, carbon tetrachloride, tetrahydrofuran, dioxane, pentane and hexane can also be applied. Hereinafter, description is made on the case where a biological sample is adopted as a specimen and the case where an observation object coated with the ionic liquid diluted with a solvent such as alcohol is adopted as a specimen.

A. Biological Sample

1. Immersion Step

First, a hydrophilic ionic liquid is prepared. Then, a water-containing biological sample is immersed in the hydrophilic ionic liquid. During immersion, the water contained in the biological sample is gradually replaced with the ionic liquid (1 to 3 hours). In this connection, specific examples of the hydrophilic ionic liquid include 1-ethyl-3-methylimidazolium tetrafluoroborate, 1-ethyl-3-methylimidazolium trifluoromethanesulfonate, 1-butyl-3-methylimidazolium tetrafluoroborate, 1-butyl-3-methylimidazolium trifluoromethanesulfonate, 1-hexyl-3-methylimidazolium bromide, 1-hexyl-3-methylimidazolium chloride or 1-decyl-3-methylimidazolium chloride.

2. Water Content Removal Step

Next, the biological sample having been immersed in the ionic liquid is placed in a vacuum chamber, and thus, the water contained in the biological sample is removed (20 minutes to 1 hour). Thus, there can be obtained a specimen in which the water content in the biological sample is replaced with the ionic liquid.

B. Specimen Prepared by Using a Diluted Ionic Liquid

Figure 6:
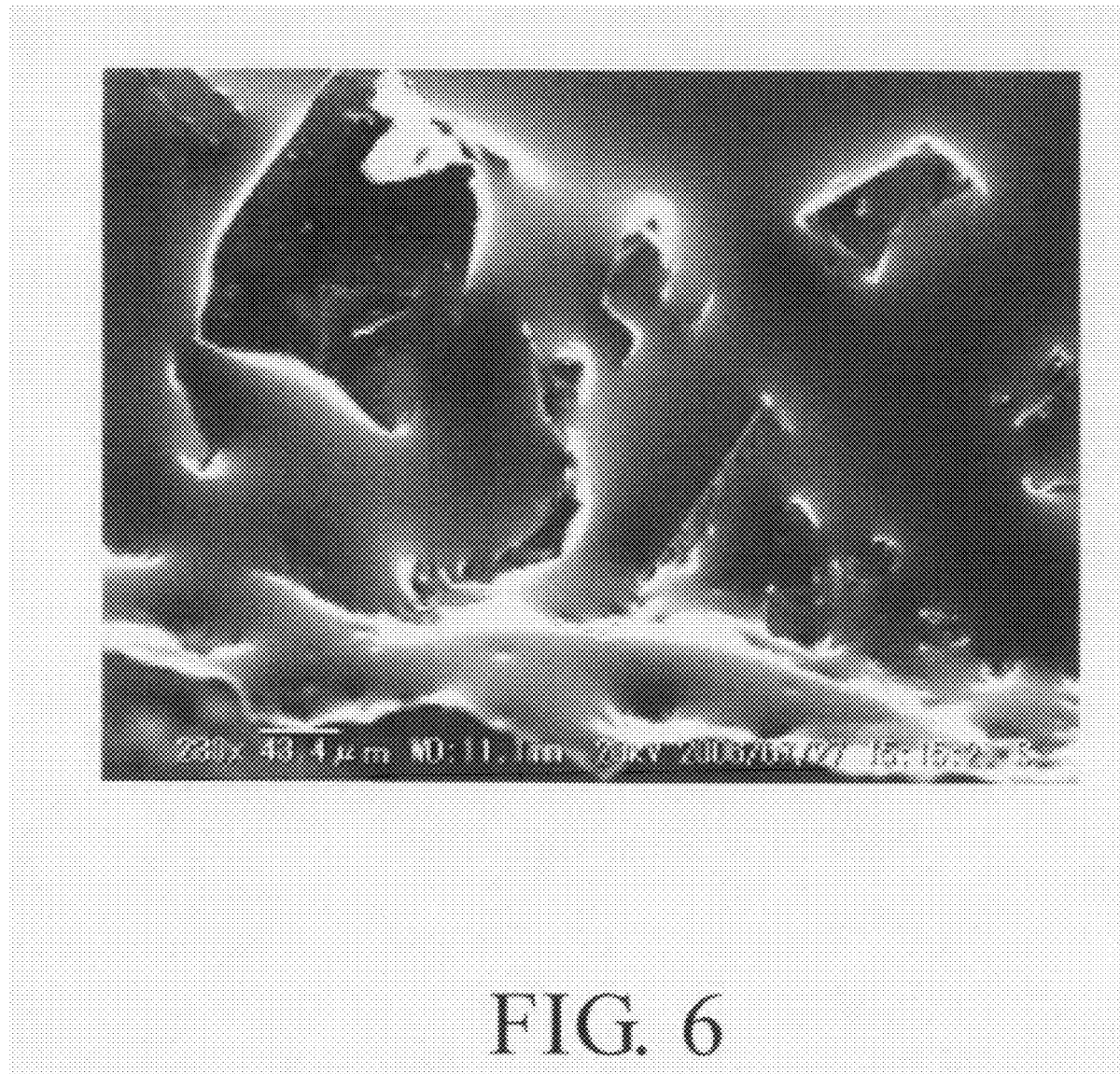
FIG. 6 is a SEM micrograph of an observation object when the observation was made on the observation object (sandpaper) coated with 1-butyl-3-methylimidazolium tetrafluoroborate (BMI-BF$_4$) without dilution with ethanol.

When an observation object having irregularities on the surface thereof or an observation object made up of aggregates of particles is observed, it is necessary to impregnate the ionic liquid into the fine structure of the observation object and to cover the fine surface of the observation object with the ionic liquid. In such a case, the ionic liquid is diluted with a solvent such as alcohol, and by applying the diluted ionic liquid to the observation object, the portion such as the interior of the fine structure or the gap between the aggregates of the particles can be coated (FIG. 6). Hereinafter, description is made on the method for preparing a specimen by using a diluted ionic liquid.

1. Dilution Step

First, an ionic liquid that includes a cation and an anion, is liquid during the observation with an electron microscope and is not volatilized at all or is scarcely volatilized under near vacuum is diluted with a solvent that is more easily volatilized than the ionic liquid. Examples of the solvent include all the inorganic and organic liquid substances that can dilute the ionic liquid; specific examples of the solvent include alcohol, benzene, toluene, acetone, methyl ethyl ketone, methylene chloride, chloroform, carbon tetrachloride, tetrahydrofuran, dioxane, pentane and hexane.

2. Coating Step

The ionic liquid diluted with the above-described solvents is impregnated into or applied to the observation object.

3. Solvent Removal Step

The observation object having been impregnated or coated with the ionic liquid diluted with the solvent is placed in the vacuum chamber, and thus the solvent is removed (a few minutes to a few dozens of minutes) to prepare a specimen. In this way, a specimen is prepared in which the surface of the observation object is coated with a thin, uniform ionic liquid film.

Figure 4:
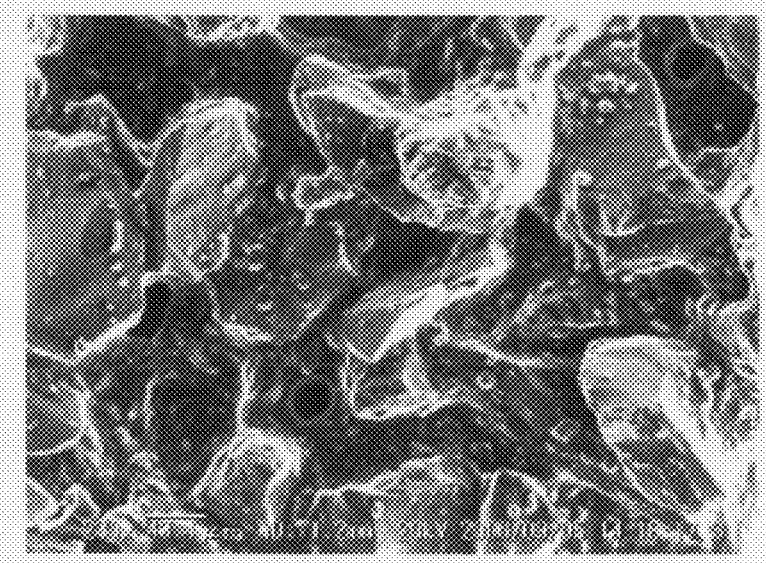
FIG. 4 is a SEM micrograph obtained when an observation was made on an observation object (sandpaper) coated with a mixture obtained by mixing ethanol with an ionic liquid, namely, 1-butyl-3-methylimidazolium tetrafluoroborate (BMI-BF$_4$).
Figure 5:
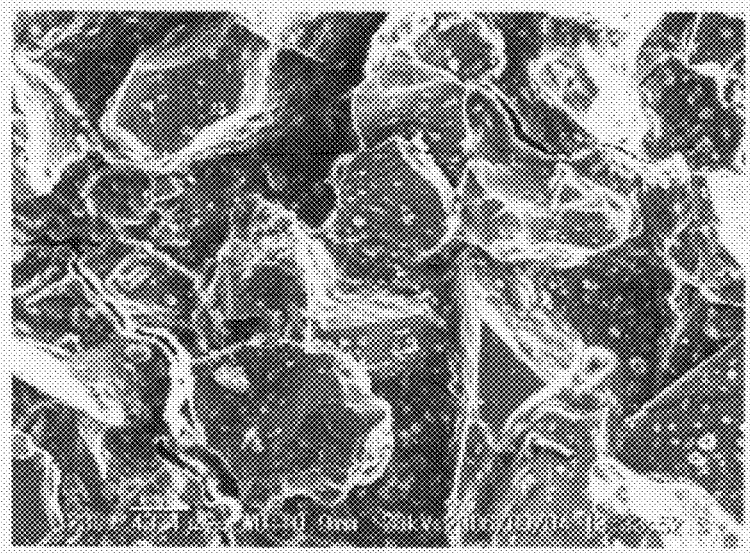
FIG. 5 is a SEM micrograph of an observation object coated with a sputtered metal.

FIG. 4 is a SEM micrograph obtained when an observation was made on an observation object (sandpaper) coated with a mixture obtained by mixing ethanol with a hydrophilic ionic liquid, namely, 1-butyl-3-methylimidazolium tetrafluoroborate ($BMI-BF_4$). When an ionic liquid is diluted with a solvent such as alcohol and the diluted ionic liquid is applied to an observation object, the ionic liquid can be impregnated into finer portions of the observation object and hence ultra-fine details of the observation object can be observed in the same manner as in the case where an observation object is prepared by metal sputtering and the observation object thus prepared is observed (FIG. 5). Accordingly, an aspect of the present invention resides in a method for preparing a specimen for observation with an electron microscope, and includes a dilution step of diluting an ionic liquid that includes a cation and an anion and is liquid during the observation with the electron microscope, with a solvent more easily volatile than the ionic liquid, a coating step of coating the observation object with the ionic liquid diluted with the solvent and a drying step of removing the solvent by placing under vacuum the observation object having been coated with the ionic liquid diluted with the solvent. FIG. 6 is a SEM micrograph of an observation object when the observation was made on the observation object (sandpaper) coated with 1-butyl-3-methylimidazolium tetrafluoroborate ($BMI-BF_4$) without dilution with ethanol. In the case where the ionic liquid mixed with ethanol is applied (FIG. 4), even the details of the side paper can be observed as compared to the case where ethanol is not mixed (FIG. 6). Accordingly, when the ionic liquid is used after diluting with the above-described solvents, the surface with fine irregularities and the surface made up of aggregates of a powder can be observed.

(Sample Observation Method)

1. Sample Preparation

In the observation with a SEM, the secondary electrons emitted from the outermost surface of a sample are detected to prepare an image, and hence the target surface intended to be observed is required to be exposed to the electron beam. For a sample for which the observation target is exposed from the beginning, a mere removal of the surface contamination may suffice; however, when the structure present in the interior is intended to be observed, it is necessary to expose the target surface by cleaning, cutting, fracturing, chemical dissolution and the like. For example, for the purpose of exposing an observation surface of a biological sample, the following sample preparation methods may be used.

1) Freeze Fracturing Method Using DMSO

A fixed sample immersed in 50% DMSO (dimethyl sulfoxide) is frozen and solidified on a metal plate cooled with liquid nitrogen, and fractured with a razor blade to expose the interior of the sample. In addition to DMSO, 100% ethanol and isoamyl acetate may also be used. According to this method, a satisfactory section can be formed.

2) Method for Removing Collagen Fiber

A sample fixed with 2% glutaraldehyde is treated with 6N—NaOH set at 60° C. for approximately 10 minutes. The collagen fiber and basement membrane are removed, and the cell surface having been covered with the connective tissue can be observed.

3) Method for Observing Collagen Fiber

A sample fixed with 2% glutaraldehyde is treated with 2N—NaOH set at 20° C. for approximately 10 minutes. The cell component is removed and the connective tissue fiber network can be observed.

4) Method for Observing Vascular Cast

Methacrylate resin monomer is injected into a blood vessel, and after the completion of resin polymerization, the soft tissue is dissolved with NaOH, and the remaining vascular cast is observed.

5) Method for Observing Intracellular Structure

The method for observing the intracellular structure is a method in which a sample subjected to a double fixation (a mixed solution of 0.5% glutaraldehyde and 0.5% formaldehyde/1% osmium) is freeze-fractured. After the double fixation, by a 0.1% osmium treatment (at 20° C., for 72 hours), portions unnecessary for observation are removed from the fractured surface, and thus the intracellular structure can be dissected.

A sample is prepared by impregnating or coating the observation surface obtained as described above with the ionic liquid. Specifically, a sample is prepared by means of the above-described method A. The contamination, the mucus culture and the like are removed with a cleaning liquid, and thereafter fixation operation is conducted. Successively, the sample impregnated or coated with the ionic liquid as described above is adhered to a SEM sample base with an adhesive, and the setting of the SEM sample base with the sample adhered thereto in the SEM system is conducted. Thereafter, the electron microscope sample chamber is evacuated to vacuum.

2. Parameter Setting

Successively, the parameters of the SEM system are set. Among these parameters, the main parameters include the acceleration voltage, the condenser lens current value, the objective aperture and the working distance. The respective parameters are significantly involved in the resolution setting, and additionally, affect the image quality, and hence these parameters are preferably set at the desired values. Hereinafter, description is made on these parameters, and the optimal set values are referred to.

1) Acceleration Voltage

The higher is the acceleration voltage value, the higher is the resolution. Additionally, the higher is the acceleration voltage value, the higher is the transmission capability of the incident electrons into the interior of the sample. By selecting 20 to 25 kV, images with higher resolution are obtained.

2) Condenser Lens Current Value

The condenser lens current value significantly changes the beam current. By increasing this current value, the resolution can be enhanced.

3) Objective Aperture

The objective aperture value changes the electron beam diameter, and hence controls the resolution. The smaller is the aperture, the higher is the resolution and simultaneously the deeper is the focal depth.

4) Working Distance

The smaller is the working distance value, the more improved is the resolution and the shallower is the focal depth. Additionally, the larger is this value, the more degraded is the resolution and the deeper is the focal depth.

3. Photographing

The above-described parameters are set, and thereafter photographing is conducted to acquire the image data. For contrasting the image, photographing is preferably conducted a plurality of times at different sample angles.

(Sample Cell)

Currently, for example, direct observation of electrochemical reactions is demanded; however, in the observation methods, hitherto having been adopted, using electron microscopes, it is necessary to dry an observation object and thereafter to coat the surface of the observation object with a metal by means of a technique such as sputtering, and hence the above-described electrochemical reactions, the variations of biological samples caused by application of electricity and other phenomena have not been able to be directly observed. However, by using the sample cell according to the present invention, the ionic liquid releases the charge built up in a biological sample, and hence the observation object can be observed without causing the charge-up.

Figure 7:
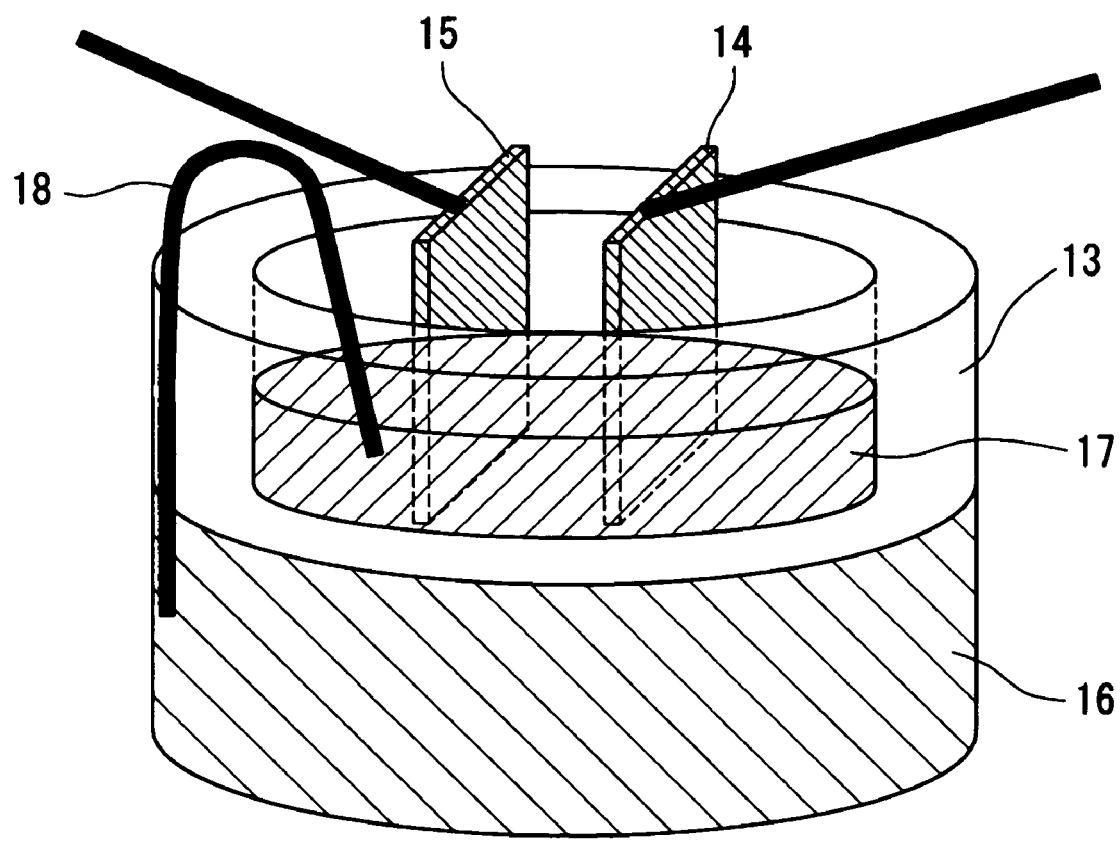
FIG. 7 is a schematic view illustrating a sample cell according to an embodiment of the present invention.

In other words, the sample cell according to the present invention is a sample cell for use in the SEM observation to be conducted while an observation object is being electrified or while a cycle of application and non-application of electricity to an observation object is being repeated; a sample cell according to an embodiment of the present invention includes an ionic liquid 17 that includes a cation and an anion and is liquid during the observation with an electron microscope, an insulating cell 13 containing the ionic liquid, a sample base 16 made of a conductor, disposed beneath the insulating cell 13, a conducting member 18 with one end thereof connected to the sample base 16 and the other end thereof disposed within the cell, and a positive electrode 14 and a negative electrode 15 immersed in the ionic liquid 17 (FIG. 7).

The ionic liquid 17 in the sample cell according to the present embodiment is the same as the ionic liquid described above. Additionally, the insulating cell 13 has a bottomed cylindrical shape so as to be able to contain the ionic liquid 17, and the sample base 16 made of a conductor is disposed beneath the bottomed cylinder. The ionic liquid 17 is conductively connected through the conducting member 18 to the sample base 16 made of a conductor, and hence the electrons emitted from the electron gun 1 in the SEM and applied to irradiation of the observation object immersed in the ionic liquid 17 are released, through the ionic liquid 17 and the conducting member 18, from the sample base 16 made of a conductor. The sample base 16 made of a conductor is capable of releasing the electrons applied to irradiation of the observation object, as described above, and the sample base 16 may be made of a metal, a semiconductor or a plastic as long as the sample base 16 has electrical conductivity. The positive electrode 14 and the negative electrode 15 can electrify the observation object, and hence, by applying electricity to the observation object, the cell permits observing the contraction and expansion and other phenomena of the observation object. For example, by repeating a cycle of application and non-application of electricity to a film of polypyrrole that is a conductive polymer, the contraction and expansion of the polypyrrole film can be observed.

Figure 8:
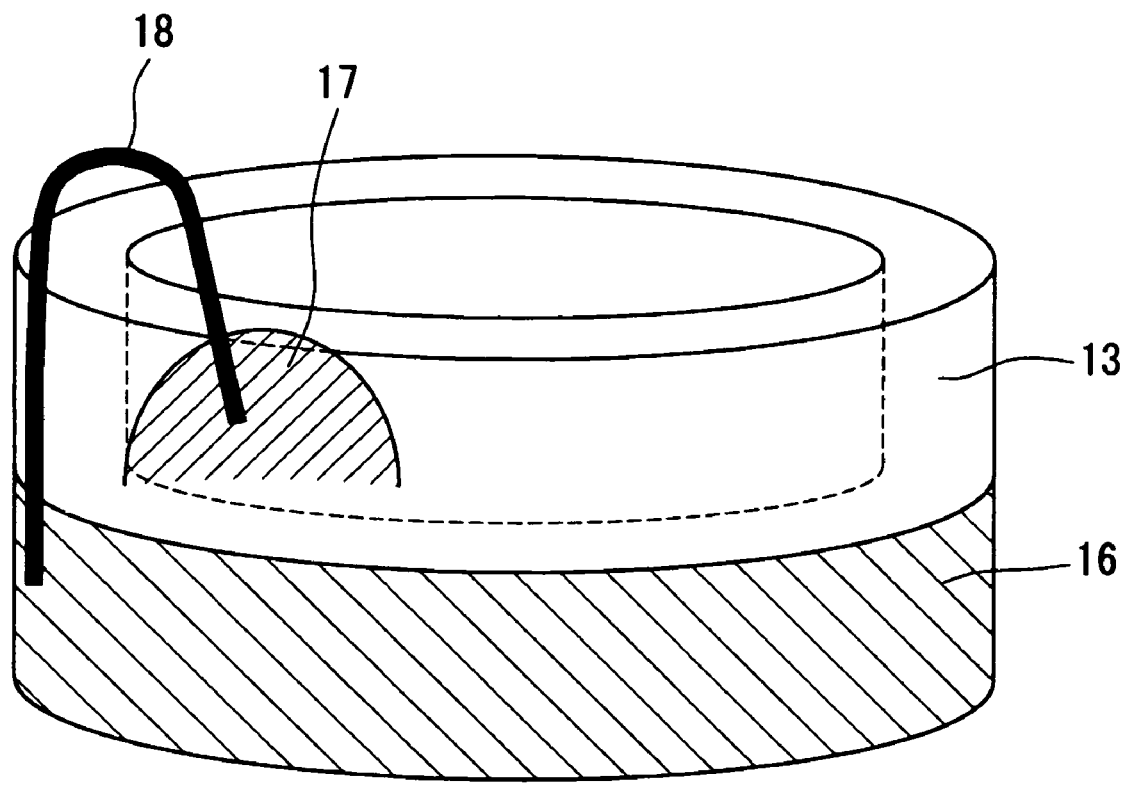
FIG. 8 is a schematic view illustrating a sample cell according to another embodiment of the present invention.

Additionally, the sample cell according to another embodiment includes an insulating cell 13 disposed on a sample base 16 made of a conductor, a conducting member 18 with one end thereof connected to the sample base 16 and the other end thereof disposed within the cell, and an ionic liquid 17 that includes a cation and an anion and is liquid during the observation with the electron microscope, and electrically connects the electrode and the other end of the conducting member to each other (FIG. 8). The insulating cell and the ionic liquid are the same as above. By application and non-application of electricity from the above-described electrodes, the contraction and expansion and other phenomena of the observation object can be observed in the same manner as in the above-described embodiment. The sample cells according to the above-described two embodiments can also be used for time-course observation of reactions such as observation of crystal growth and synthesis of nanomaterials.

(Electron Microscope Equipped with an Insulating Cell Capable of Containing an Ionic Liquid)

When an ionic liquid is impregnated into an observation object, because the ionic liquid has nonvolatility and further, electrical conductivity as described above, the observation object can be observed while the charge-up is being prevented. Additionally, when a positive electrode and a negative electrode are connected to the observation object, the behavior caused by electrifying the observation object can be observed.

Accordingly, an aspect of the present invention resides in an electron microscope used for observation of a specimen, including a vacuum chamber that houses the specimen and is evacuated to vacuum, an insulating cell that is housed in the vacuum chamber and is capable of containing an ionic liquid that is liquid during the observation with the electron microscope, a positive electrode and a negative electrode immersed in the ionic liquid filled in the insulating cell, an electron gun that irradiates the specimen with an electron beam and a detector that detects the secondary electrons generated by irradiating the specimen with the electrons from the electron gun.

Figure 2:
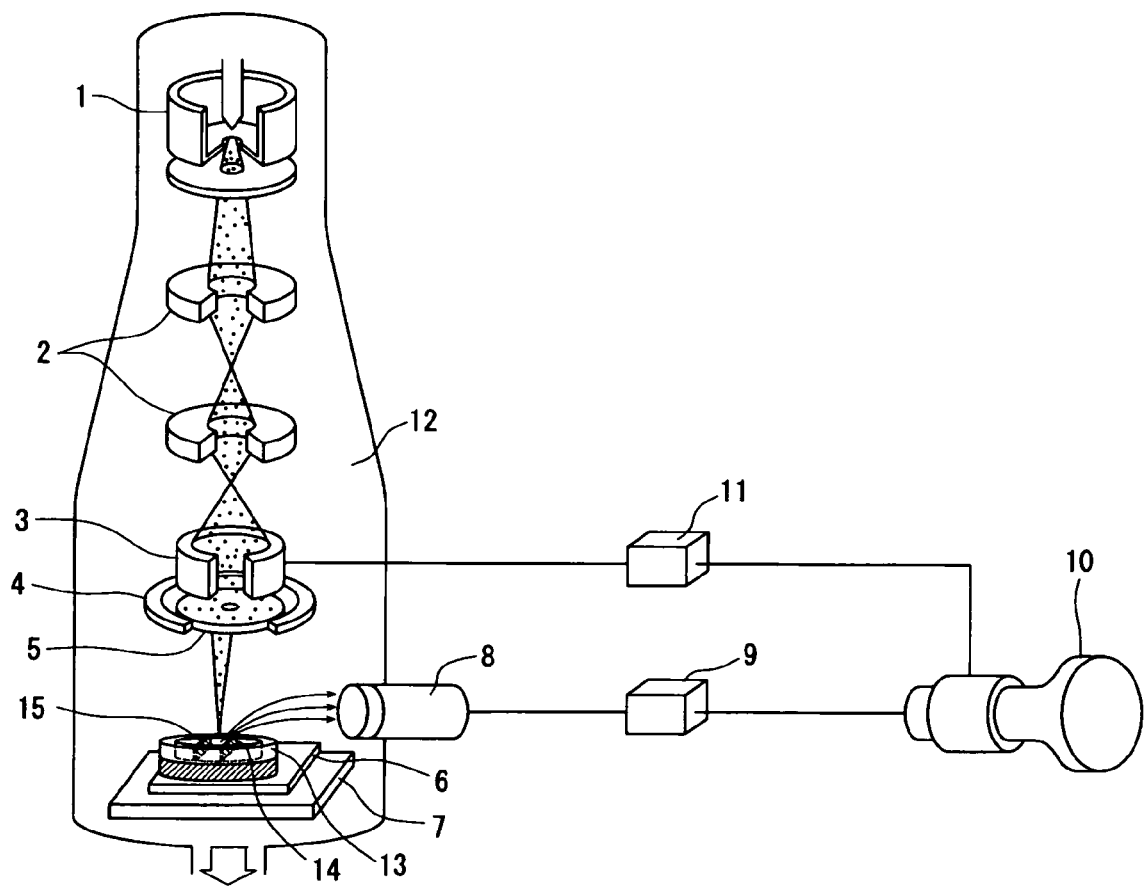
FIG. 2 is a schematic view illustrating a SEM system.
Figure 3:
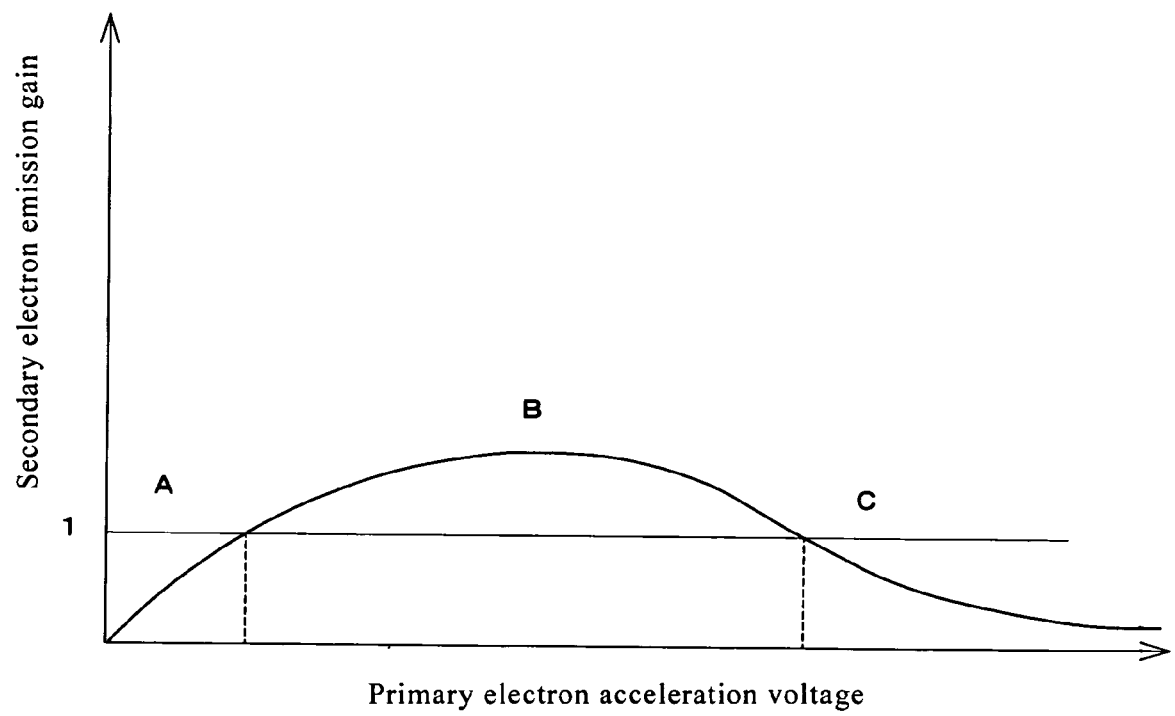
FIG. 3 is a graph showing a relation between the primary electron acceleration voltage and the secondary electron emission gain.

FIG. 2 illustrates an example of the SEM system according to the present invention. The SEM system has a vacuum chamber 12, an insulating cell 13 capable of containing an ionic liquid, a positive electrode 14, a negative electrode 15, an electron gun 1, condenser lenses 2, a scanning coil 3, an objective lens 4 and an objective-lens aperture 5, and further includes an electron optical system that scans a sample placed on the top of a basal plate 6, a stage 7 on the top of which the basal plate 6 is placed, a detector 8 that detects the secondary electrons from the sample, an image amplifier 9 that amplifies the output from the detector 8, a display unit 10 including a Brown tube (CRT) and a scanning circuit 11 for driving the electron optical system.

An electron beam emitted from the electron gun 1 passes through the condenser lenses 2, the scanning coil 3 and the objective lens 4, and then is applied to irradiation of the sample placed on the top of the stage 7. The detector 8 detects the secondary electrons generated from the sample by the scanning of the electron beam irradiation. The detection signal from the detector 8 is made pass through the image amplifier 9 and displayed on the display unit 10.

The vacuum chamber 12 of the electron microscope according to the present invention is evacuated to a high vacuum condition after the sample observation cell has been inserted into the vacuum chamber 12. In the upper portion of the vacuum chamber 12, the electron gun 1 for irradiating the observation object with electrons is provided; and the sample observation cell 13 is disposed nearly directly below the electron gun 1, and the observation object in the cell is irradiated with the electrons from the electron gun. Additionally, the electron gun 1 is for the purpose of irradiating the observation object in the sample cell with electrons, and is capable of irradiating with electrons having an energy falling in a range from a few eV to a few dozens of eV. Further, the detector 8 for the secondary electrons is for the purpose of detecting the secondary electrons generated by the irradiation with the primary electrons, and is capable of collecting the secondary electrons by applying an electric field to the generated secondary electrons. Additionally, the insulating cell 13, and the positive electrode 14 and the negative electrode 15 are the same as described above.

As described above, description has been made on the application of the ionic liquid to the SEM sample; however, the ionic liquid of the present invention may be applied to a SPM sample. In other words, the present invention includes the ionic liquid as an essential component, and the ionic liquid may be an electrical conductivity-imparting liquid medium, for use in a scanning probe microscope (hereinafter referred to as SPM), which is impregnated into the entirety of a sample for use in a scanning probe microscope or applied to the scanning surface of the sample concerned so as to impart electrical conductivity at least to the scanning surface. Herewith, even for a long time observation, the ionic liquid impregnated into the SPM sample is not evaporated and thus the shape of the sample can be maintained for a long time.

Example 1

Hereinafter, Examples according to the present invention are described. The following Examples are for the purpose of illustration and it is understood that the present invention is not to be limited to following Examples.

In Example 1, hydrophilic 1-butyl-3-methylimidazolium tetrafluoroborate (BMI-BF$_4$) was used.

Figure 9:
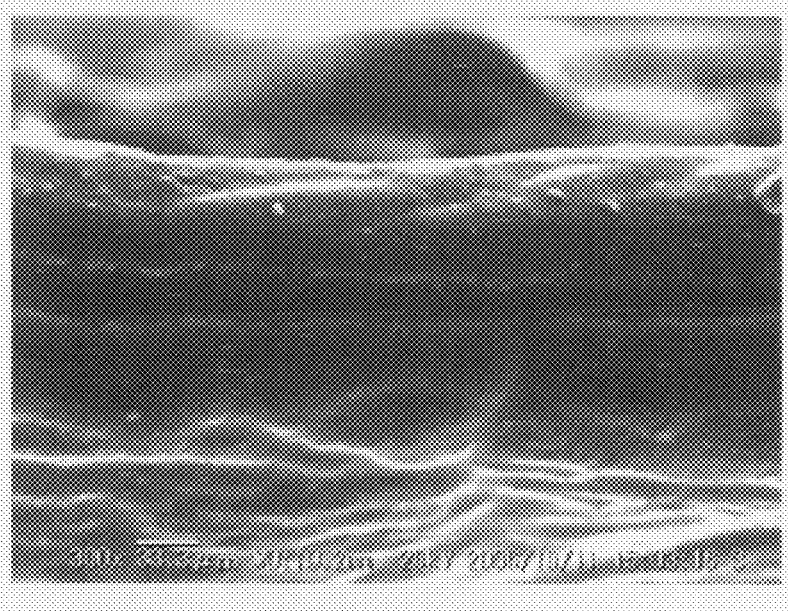
FIG. 9 is a SEM micrograph (300×) of a specimen of wakame (*Undaria pinnatifida*) impregnated with hydrophilic BMI-BF$_4$.

First, a dried specimen of wakame (*Undaria pinnatifida*) was rehydrated with water. Thereafter, the rehydrated specimen of wakame was immersed in hydrophilic BMI-BF$_4$ for 2 hours, the water contained in the specimen of wakame was slowly replaced with BMI-BF$_4$. Thereafter, the specimen of wakame was placed under near vacuum (2 mmHg or less) for 30 minutes and vacuum dried. FIG. 9 is a SEM micrograph (300×) of a specimen of wakame impregnated with BMI-BF$_4$, observed with a SEM. An observation method according to the present invention was able to observe a rehydrated specimen of wakame, namely, a wet specimen of wakame.

Figure 10:
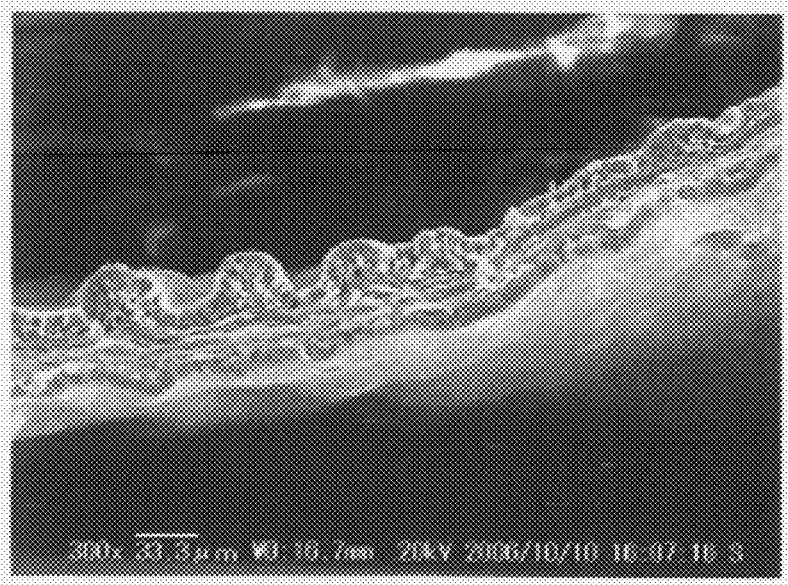
FIG. 10 is a SEM micrograph (300×) of a dried specimen of wakame (*Undaria pinnatifida*) sputtered with Au in a conventional manner.

FIG. 10 is a SEM micrograph (300×) obtained by sputtering gold on a dried specimen of wakame in a conventional manner, and by thereafter observing the specimen of wakame with a SEM.

The specimen of wakame observed by the method according to the present invention was as approximately 3.5 times thick as a specimen of wakame observed by a conventional method. Additionally, in the specimen of wakame observed by a conventional method, pleat-shaped portions were observed; on the contrary, in the specimen of wakame observed by the method according to the present invention, no pleat-shaped portions were observed, but the shape originally possessed by wakame was observed.

Figure 11:
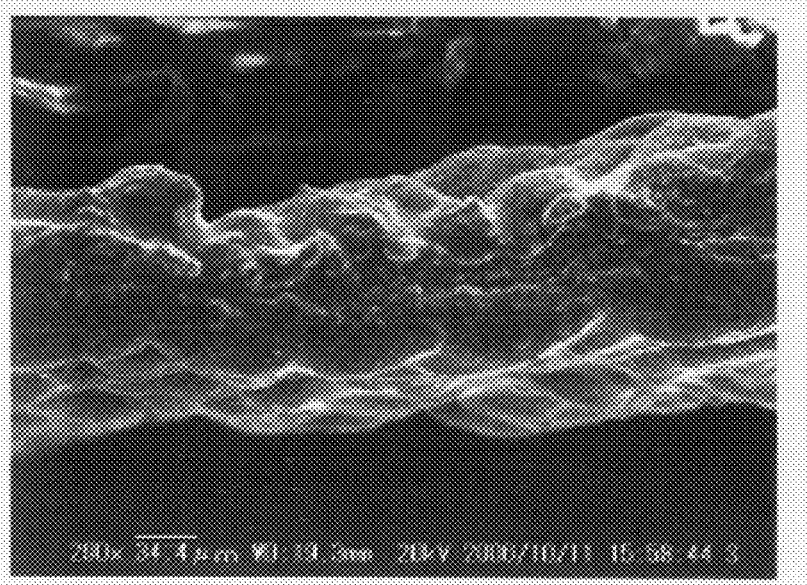
FIG. 11 is a SEM micrograph (300×) of a specimen of wakame (*Undaria pinnatifida*) impregnated with hydrophobic BMI-TFSI.

FIG. 11 is a SEM micrograph (300×) obtained by observing, with a SEM, a specimen of wakame (*Undaria pinnatifida*) impregnated with hydrophobic 1-butyl-3-methylimidazolium bis(trifluoromethane sulfonyl)imide (BMI-TFSI). In this case, as compared with the specimen of wakame impregnated with the hydrophilic ionic liquid, the thickness of the specimen of wakame was made thinner and pleat-shaped portions were abundantly observed. This is probably because the water contained in the specimen of wakame was not replaced with the hydrophobic ionic liquid in a satisfactory manner. Accordingly, when a biological material containing a large water content is observed, it is preferable to use a hydrophilic ionic liquid.

Example 2

In Example 2, 1-ethyl-3-methylimidazolium tetrafluoroborate was used as an ionic liquid, and this ionic liquid was impregnated into a sample of star sand and the thus impregnated sample of star sand was observed with a SEM system. As the ionic liquid, 1-ethyl-3-methylimidazolium tetrafluoroborate manufactured by Lancaster Inc. was used. First, the contamination and the like attached to the sample of star sand were removed with a cleaning liquid, and thereafter the sample (star sand) was adhered and fixed to the SEM sample base with an adhesive, and successively the sample was impregnated with 1-ethyl-3-methylimidazolium tetrafluoroborate. The setting of the SEM sample base was conducted in the SEM system. Thereafter, the electron microscope sample chamber was evacuated to vacuum. The SEM acceleration voltage was set at 20 kV and the working distance (WD) was set at 21.1 mm. The star sand was observed under the above-described conditions and an image of the star sand was able to be obtained.

FIG. 1 is a SEM micrograph obtained by photographying a sample of star sand impregnated with the ionic liquid (left) as described above and a sample of star sand not impregnated with the ionic liquid (right) arranged in parallel to each other. In the case of the star sand not impregnated with the ionic liquid (right), the image was found to be white due to charge-up. However, in the case of the star sand impregnated with the ionic liquid (left), charge-up was able to be prevented although the star sand was formed of insulating materials. Additionally, the above-described ionic liquid was not volatilized even under vacuum, and hence a satisfactory observation for a long time was enabled.

Example 3

In Example 3, 1-butyl-3-methylimidazolium tetrafluoroborate was used as an ionic liquid, and this ionic liquid was impregnated into a sample of star sand and the thus impregnated sample of star sand was observed with a SEM system. In present Example 3, the operations were conducted in the same manner as in Example 2 except that 1-butyl-3-methylimidazolium tetrafluoroborate was used in place of 1-ethyl-3-methylimidazolium tetrafluoroborate. Also in this Example 3, a satisfactory observation was enabled in the same manner as described above.

Example 4

In Example 4, 1-ethyl-3-methylimidazolium bis(trifluoromethanesulfonyl)imide was used as an ionic liquid, and this ionic liquid was impregnated into a sample of star sand and the thus impregnated sample of star sand was observed with a SEM system. In present Example 4, the operations were conducted in the same manner as in Example 1 except that 1-ethyl-3-methylimidazolium bis(trifluoromethanesulfonyl) imide was used in place of 1-ethyl-3-methylimidazolium tetrafluoroborate. Also in this Example 4, a satisfactory observation was enabled in the same manner as in Example 2.

Example 5

In Example 5, 1-butyl-3-methylimidazolium bis(trifluoromethanesulfonyl)imide was used as an ionic liquid, and this ionic liquid was impregnated into a sample of star sand and the thus impregnated sample of star sand was observed with a SEM system. In present Example 5, the operations were conducted in the same manner as in Example 2 except that 1-butyl-3-methylimidazolium bis(trifluoromethanesulfonyl) imide was used in place of 1-ethyl-3-methylimidazolium tetrafluoroborate. Also in this Example 5, a satisfactory observation was enabled in the same manner as in Example 2.

Example 6

In Example 6, 1-butyl-3-methylimidazolium hexafluorophosphate was used as an ionic liquid, and this ionic liquid was impregnated into a sample of star sand and the thus impregnated sample of star sand was observed with a SEM system. In present Example 6, the operations were conducted in the same manner as in Example 2 except that 1-butyl-3-methylimidazolium hexafluorophosphate was used in place of 1-ethyl-3-methylimidazolium tetrafluoroborate. Also in this Example 6, a satisfactory observation was enabled in the same manner as in Example 2.

Example 7

In Example 7, trimethyl-n-propylammonium bis(trifluoromethanesulfonyl)imide was used as an ionic liquid, and this ionic liquid was impregnated into a sample of star sand and the thus impregnated sample of star sand was observed with a SEM system. In present Example 7, the operations were conducted in the same manner as in Example 2 except that trimethyl-n-propylammonium bis(trifluoromethanesulfonyl) imide was used in place of 1-ethyl-3-methylimidazolium tetrafluoroborate. Also in this Example 7, a satisfactory observation was enabled in the same manner as in Example 2.

Example 8

In Example 8, a film of polypyrrole, a conductive polymer, was formed on the surface of one of thin film metal electrodes, and the contraction and expansion of the film of polypyrrole were observed in the case where application and non-application of electricity to the film of polypyrrole was conducted.

Figure 12:
FIG. 12 is a SEM micrograph of a film of polypyrrole with electricity applied thereto.
Figure 13:
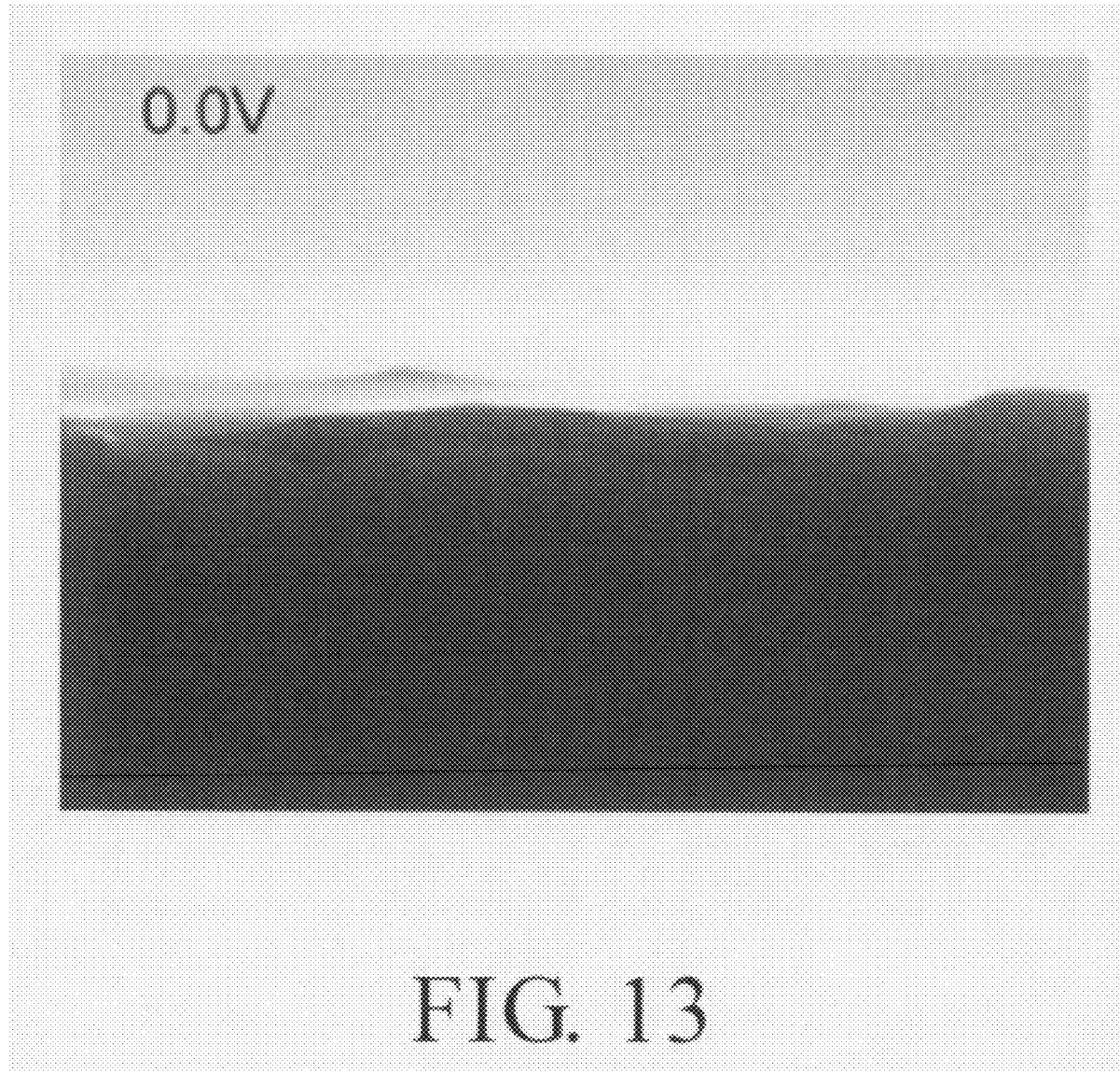
FIG. 13 is a SEM micrograph of a film of polypyrrole without electricity applied thereto.

First, two Pt electrodes, namely a working electrode (WE) and a counter electrode (CE) were immersed in an electrolytic solution composed of 0.1-M pyrrole and 0.1-M sodium p-toluenesulfonate in an insulating cell, a constant current of 3 mA was applied to these two electrodes for 2 hours to perform an electrolytic polymerization to form a film of polypyrrole on the surface of one of the platinum plates. Thereafter, the film of polypyrrole was cleaned with ultrapure water and acetonitrile, and successively, an ionic liquid, $BMI-BF_4$, was added as an electrolytic solution. Then, for the purpose of removing the water content, the whole cell was placed under vacuum for 2 hours to be vacuum dried. The cell was placed in a SEM system, and the film of polypyrrole was observed with the SEM system. FIG. 12 is a SEM micrograph of the film of polypyrrole in the cell with electricity applied thereto, and FIG. 13 is a SEM micrograph of the film of polypyrrole without electricity applied thereto. The thickness of the film of polypyrrole with electricity applied thereto is larger than that without electricity applied thereto, and the increment of the film thickness reaches 1% to 20% of the total thickness of the film of polypyrrole found without electricity applied thereto.

INDUSTRIAL APPLICABILITY

The electrical conductivity-imparting medium that contains an ionic liquid, according to the present invention, is used when a sample is observed with a SEM, a TEM or the like, for the purpose of imparting electrical conductivity to the sample in such a way that the electrical conductivity-imparting medium is impregnated into the sample to be observed with these electron microscope or applied to the observation surface of the sample to be observed with these electron microscope.

The invention claimed is:

1. A charge-up preventing liquid medium for electron microscope, characterized in that the liquid medium comprises as an essential component thereof an ionic liquid that is composed of a cation and an anion and is not volatilized at all or is scarcely volatilized under vacuum, and is impregnated into the entirety of a sample for a scanning electron microscope (SEM) or a sample for a transmission electron microscope (TEM) or applied to the electron irradiation surface of the sample to impart electrical conductivity at least to the electron irradiation surface.

2. The charge-up preventing liquid medium for electron microscope according to claim 1, wherein the ionic liquid is represented by a general formula: $K^+A^-$ (in the formula, $K^+$ is N-alkylimidazolium cation or a quaternary ammonium cation, and $A^-$ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

3. The charge-up preventing liquid medium for electron microscope according to claim 1, wherein the ionic liquid is represented by a general formula: $K^+A^-$ (in the formula, $K^+$ is a quaternary ammonium cation or a quaternary phosphonium cation, and $A^-$ is bis(halogenated alkylsulfonyl)imide anion or bis(halogenated sulfonyl)imide anion).

4. The charge-up preventing liquid medium for electron microscope according to claim 1, wherein the ionic liquid is represented by a general formula: $K^+A^-$ (in the formula, $K^+$ is a cation selected from the group consisting of

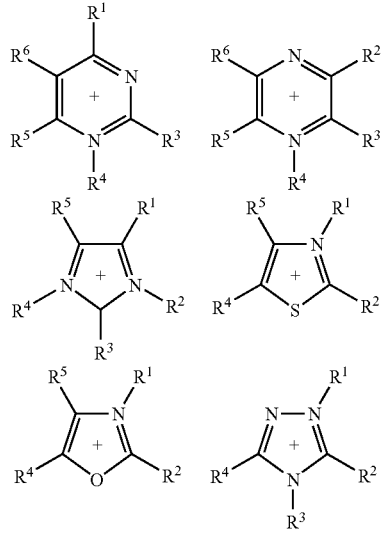

and $A^-$ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

5. The charge-up preventing liquid medium for electron microscope according to claim 1, wherein the ionic liquid is represented by a general formula: $K^+A^-$ (in the formula, $K^+$ is benzyldimethylalkylammonium cation or alkylpyridinium cation, and $A^-$ is bis-2-ethylhexyl sulfosuccinate anion).

6. A specimen for observation with an electron microscope, comprising:
an observation object; and
an ionic liquid that includes a cation and an anion and is liquid during the observation with the electron microscope.

7. The specimen according to claim 6, wherein the ionic liquid is applied to the electron irradiation surface, to be irradiated with electrons, of the observation object.

8. The specimen according to claim 6, wherein the ionic liquid is impregnated into the observation object.

9. The specimen according to claim 6, wherein the observation object is a biological sample and at least part of the water contained in the biological sample is replaced with the ionic liquid.

10. The specimen according to claim 6, wherein the observation object comprises a fine structure on the surface thereof and the ionic liquid is applied to the fine structure.

11. The specimen according to claim 6, wherein the observation object comprises aggregates of particles and the ionic liquid is applied to the electron irradiation surface of each of the particles.

12. The specimen according to claim 6, wherein the observation object contains a hydrophilic ionic liquid having high affinity for water.

13. The specimen according to claim 6, wherein the observation object contains a hydrophobic ionic liquid having low affinity for water.

14. The specimen according to claim 6, wherein the ionic liquid is represented by a general formula: $K^+A^-$ (in the formula, $K^+$ is N-alkylimidazolium cation, a quaternary ammonium cation, and $A^-$ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

15. The specimen according to claim 6, wherein the ionic liquid is represented by a general formula: $K^+A^-$ (in the formula, $K^+$ is a quaternary ammonium cation or a quaternary phosphonium cation, and $A^-$ is bis(halogenated alkylsulfonyl)imide anion or bis(halogenated sulfonyl)imide anion).

16. The specimen according to claim 6, wherein the ionic liquid is represented by a general formula: $K^+A^-$ (in the formula, $K^+$ is a cation selected from the group consisting of

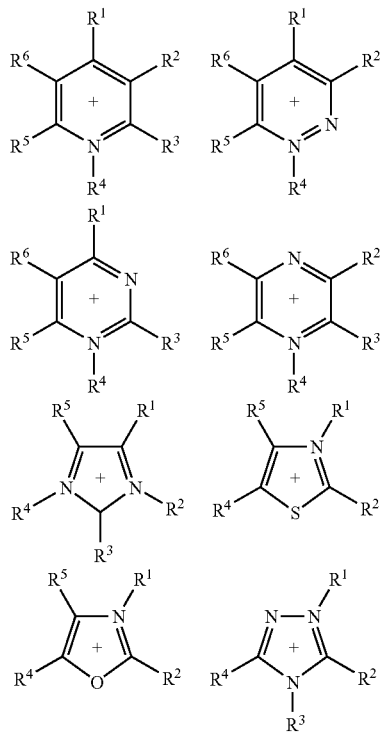

and $A^-$ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

17. The specimen according to claim 6, wherein the ionic liquid is represented by a general formula: $K^+A^-$ (in the formula, $K^+$ is benzyldimethylalkylammonium cation or alkylpyridinium cation, and $A^-$ is bis-2-ethylhexyl sulfosuccinate anion).

18. A method for preparing a specimen for observation with an electron microscope, comprising:
an immersion step of immersing a water-containing biological sample in an ionic liquid that includes a cation and an anion and is liquid during the observation with the electron microscope; and
a drying step of removing the water contained in the biological sample by placing under vacuum the biological sample having been immersed in the ionic liquid.

19. A method for preparing a specimen for observation with an electron microscope, comprising:
a dilution step of diluting an ionic liquid that includes a cation and an anion and is liquid during the observation with the electron microscope, with a solvent more easily volatile than the ionic liquid,
a coating step of coating the observation object with the ionic liquid diluted with the solvent; and a drying step of removing the solvent by placing under vacuum the observation object having been coated with the ionic liquid diluted with the solvent.

20. The method for preparing a specimen according to claim 18 or 19, wherein the ionic liquid is represented by a general formula: $K^+A^-$ (in the formula, $K^+$ is N-alkylimidazolium cation or a quaternary ammonium cation, and $A^-$ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

21. The method for preparing a specimen according to claim 18 or 19, wherein the ionic liquid is represented by a general formula: $K^+A^-$ (in the formula, $K^+$ is a quaternary ammonium cation or a quaternary phosphonium cation, and $A^-$ is bis(halogenated alkylsulfonyl)imide anion or bis(halogenated sulfonyl)imide anion).

22. The method for preparing a specimen according to claim 18 or 19, wherein the ionic liquid is represented by a general formula: $K^+A^-$ (in the formula, $K^+$ is a cation selected from the group consisting of

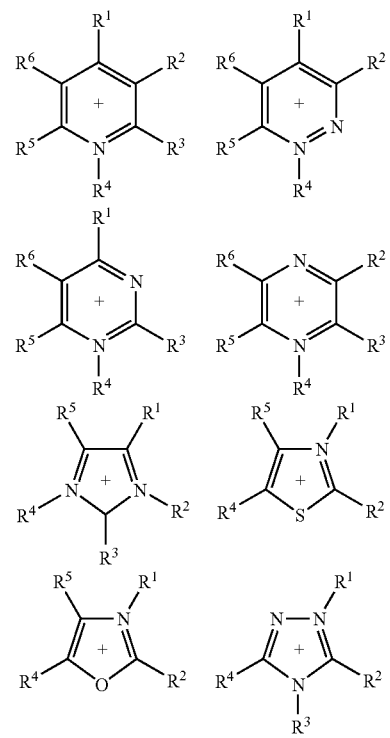

and $A^-$ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

23. The method for preparing a specimen according to claim 18 or 19, wherein the ionic liquid is represented by a general formula: $K^+A^-$ (in the formula, $K^+$ is benzyldimethylalkylammonium cation or alkylpyridinium cation, and $A^-$ is bis-2-ethylhexyl sulfosuccinate anion).

24. A sample cell used for observation of a specimen with an electron microscope, comprising:
an ionic liquid that includes a cation and an anion and is liquid during the observation with the electron microscope;

an insulating cell containing the ionic liquid;

a positive electrode and a negative electrode immersed in the ionic liquid; and a conducting member with one end thereof disposed within the cell.

25. A sample cell used for observation of a specimen with an electron microscope, comprising:

an insulating cell disposed on a sample base made of a conductor;

an electrode disposed within the insulating cell;

a conducting member with one end thereof connected to the sample base and the other end thereof disposed within the cell; and an ionic liquid that includes a cation and an anion and is liquid during the observation with the electron microscope and electrically connects the electrode and said the other end of the conducting member to each other.

26. The sample cell according to claim 24 or 25, wherein the ionic liquid is represented by a general formula: $K^+A^-$ (in the formula, $K^+$ is N-alkylimidazolium cation or a quaternary ammonium cation, and $A^-$ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

27. The sample cell according to claim 24 or 25, wherein the ionic liquid is represented by a general formula: $K^+A^-$ (in the formula, $K^+$ is a quaternary ammonium cation or a quaternary phosphonium cation, and $A^-$ is bis(halogenated alkylsulfonyl)imide anion or bis(halogenated sulfonyl)imide anion).

28. The sample cell according to claim 24 or 25, wherein the ionic liquid is represented by a general formula: $K^+A^-$ (in the formula, $K^+$ is a cation selected from the group consisting of

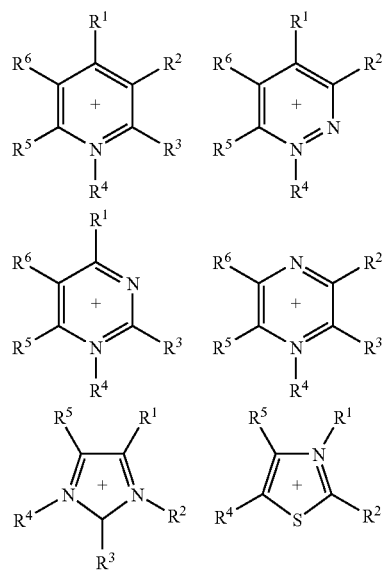

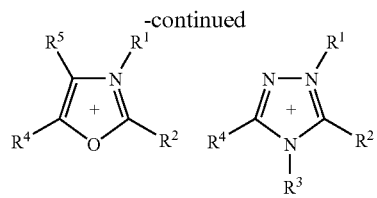

and $A^-$ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

29. The sample cell according to claim 24 or 25, wherein the ionic liquid is represented by a general formula: $K^+A^-$ (in the formula, $K^+$ is benzyldimethylalkylammonium cation or alkylpyridinium cation, and $A^-$ is bis-2-ethylhexyl sulfosuccinate anion).

30. An electron microscope used for observation of a specimen, comprising:

a vacuum chamber that houses the specimen and is evacuated to vacuum;

an insulating cell that is housed in the vacuum chamber and is capable of containing an ionic liquid that is liquid during the observation with the electron microscope;

a positive electrode and a negative electrode immersed in the ionic liquid filled in the insulating cell;

an electron gun that irradiates the specimen with an electron beam; and a detector that detects the secondary electrons generated by irradiating the specimen with the electrons from the electron gun.

31. The electron microscope according to claim 30, wherein the ionic liquid is represented by a general formula: $K^+A^-$ (in the formula, $K^+$ is N-alkylimidazolium cation or a quaternary ammonium cation, and $A^-$ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

32. The electron microscope according to claim 30, wherein the ionic liquid is represented by a general formula: $K^+A^-$ (in the formula, $K^+$ is a quaternary ammonium cation or a quaternary phosphonium cation, and $A^-$ is bis(halogenated alkylsulfonyl)imide anion or bis(halogenated sulfonyl)imide anion).

33. The electron microscope according to claim 30, wherein the ionic liquid is represented by a general formula: $K^+A^-$ (in the formula, $K^+$ is a cation selected from the group consisting of

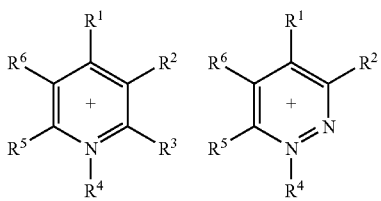

-continued

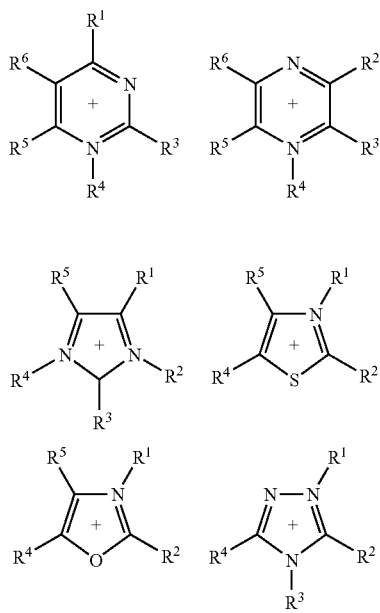

and A⁻ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

34. The electron microscope according to claim 30, wherein the ionic liquid is represented by a general formula: K⁺A⁻ (in the formula, K⁺ is benzyldimethylalkylammonium cation or alkylpyridinium cation, and A⁻ is bis-2-ethylhexyl sulfosuccinate anion).

35. A method for observing a sample with an electron microscope, characterized by comprising:
   a step of imparting electrical conductivity at least to the observation surface of an observation object by impregnating the observation object with an ionic liquid that is composed of a cation and an anion and is not volatilized at all or is scarcely volatilized under vacuum, or by coating the observation surface of the observation object with the ionic liquid; and
   a step of obtaining an image of the observation object by irradiating with electrons the observation object having been impregnated or coated with the ionic liquid as described above and by detecting the secondary electrons or the transmitted electrons due to the irradiating electrons.

36. A method for observing a sample with an electron microscope, comprising:
   a step of immersing an observation object in an ionic liquid that includes a cation and an anion and is liquid during the observation with the electron microscope;
   a step of bringing a positive electrode and a negative electrode into contact with the observation object; and
   a step of obtaining an image of the observation object by irradiating the observation object with electrons while electricity is being applied to the observation object and by detecting the secondary electrons or the transmitted electrons due to the irradiating electrons.

37. A method for observing a sample with an electron microscope, comprising:
   a step of immersing an observation object in an ionic liquid that includes a cation and an anion and is liquid during the observation with the electron microscope;
   a water content removal step in which a biological sample having been immersed in the ionic liquid is placed under vacuum and the water contained in the biological sample is removed; and
   a step of obtaining an image of the observation object by irradiating with electrons the observation object having been impregnated or coated with the ionic liquid and by detecting the secondary electrons or the transmitted electrons due to the irradiating electrons.

38. A method for observing a sample with an electron microscope, comprising:
   a dilution step of diluting an ionic liquid that includes a cation and an anion and is liquid during the observation with the electron microscope, with a solvent more easily volatile than the ionic liquid,
   a coating step of coating the observation object with the ionic liquid diluted with the solvent;
   a water content removal step of removing the solvent by placing under vacuum the observation object having been coated with the ionic liquid diluted with the solvent; and
   a step of obtaining an image of the observation object by irradiating with electrons the observation object having been coated with the ionic liquid and by detecting the secondary electrons or the transmitted electrons due to the irradiating electrons.

39. The method for observing a sample according to claim 38, wherein the solvent is at least one solvent selected from the group consisting of alcohol, acetone, methyl ethyl ketone, methylene chloride, chloroform, carbon tetrachloride, tetrahydrofuran, dioxane, pentane and hexane.

40. The method for observing a sample according to any one of claims 35 to 39, wherein the ionic liquid is represented by a general formula: K⁺A⁻ (in the formula, K⁺ is N-alkylimidazolium cation or a quaternary ammonium cation, and A⁻ is a tetrazole compound anion, a triazole compound anion, tetrafluoroborate anion, tetrachloroborate anion, tetraalkylborate anion, tetraarylborate anion, hexafluorophosphate anion, hexafluoroantimonate anion, fluorosulfonate anion, alkylsulfonate anion, fluoroalkylsulfonate anion, bis(fluoroalkylsulfonyl)imide anion or arenesulfonate anion).

41. The method for observing a sample according to any one of claims 35 to 39, wherein the ionic liquid is represented by a general formula: K⁺A⁻ (in the formula, K⁺ is a quaternary ammonium cation or a quaternary phosphonium cation, and A⁻ is bis(halogenated alkylsulfonyl)imide anion or bis(halogenated sulfonyl)imide anion).

42. The method for observing a sample according to any one of claims 35 to 39, wherein the ionic liquid is represented by a general formula: K⁺A⁻ (in the formula, K⁺ is a cation selected from the group consisting of

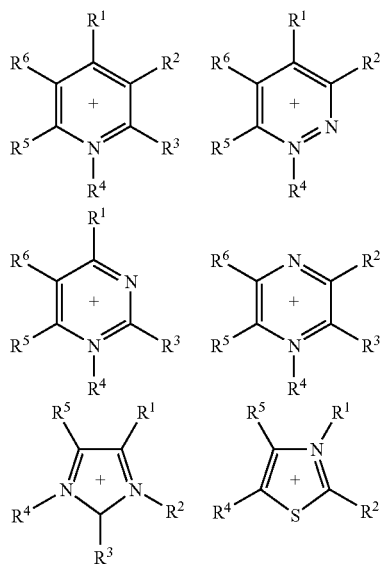

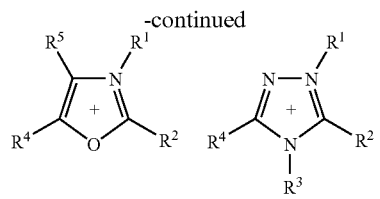

and A⁻ is an anion represented by $[B(OR^7)_n(OR^8)_m(OR^9)_o(OR^{10})_p]^-$ (B is boron, and $R^7$ to $R^{10}$ are each a hydrogen atom or a $C_{1-10}$ alkyl group)).

43. The method for observing a sample according to any one of claims 35 to 39, wherein the ionic liquid is represented by a general formula: K⁺A⁻ (in the formula, K⁺ is benzyldimethylalkylammonium cation or alkylpyridinium cation, and A⁻ is bis-2-ethylhexyl sulfosuccinate anion).

\* \* \* \* \*